United States Patent
Kim et al.

(10) Patent No.: US 10,123,841 B2
(45) Date of Patent: Nov. 13, 2018

(54) METHOD FOR GENERATING INSERTION TRAJECTORY OF SURGICAL NEEDLE

(71) Applicants: THE ASAN FOUNDATION, Seoul (KR); UNIVERSITY OF ULSAN FOUNDATION FOR INDUSTRY COOPERATION, Ulsan (KR)

(72) Inventors: Nam Kug Kim, Seoul (KR); Sang Min Lee, Seoul (KR); Min Ho Lee, Seoul (KR); Joon Beom Seo, Soeul (KR); Se Youn Park, Seoul (KR)

(73) Assignees: THE ASAN FOUNDATION, Seoul (KR); UNIVERSITY OF ULSAN FOUNDATION FOR INDUSTRY COOPERATION, Ulsan (KR)

(*) Notice: Subject to any disclaimer, the term of this patent is extended or adjusted under 35 U.S.C. 154(b) by 0 days.

(21) Appl. No.: 15/107,401

(22) PCT Filed: Dec. 23, 2014

(86) PCT No.: PCT/KR2014/012761
§ 371 (c)(1),
(2) Date: Jun. 22, 2016

(87) PCT Pub. No.: WO2015/099427
PCT Pub. Date: Jul. 2, 2015

(65) Prior Publication Data
US 2017/0000567 A1    Jan. 5, 2017

(30) Foreign Application Priority Data

Dec. 23, 2013 (KR) .................. 10-2013-0161279
Dec. 23, 2013 (KR) .................. 10-2013-0161284
Dec. 23, 2013 (KR) .................. 10-2013-0161288

(51) Int. Cl.
*A61B 34/10* (2016.01)
*A61B 6/03* (2006.01)
(Continued)

(52) U.S. Cl.
CPC .............. *A61B 34/10* (2016.02); *A61B 6/03* (2013.01); *A61B 10/0233* (2013.01);
(Continued)

(58) Field of Classification Search
CPC ... G06T 17/005; G06T 19/20; A61B 10/0233; A61B 17/3403; A61B 2034/107;
(Continued)

(56) References Cited

U.S. PATENT DOCUMENTS 6,487,431 B1   11/2002   Iwano et al. .................. 600/407
8,535,336 B2    9/2013   Trovato ........................ 606/130
(Continued)

FOREIGN PATENT DOCUMENTS

JP    2011-525827      9/2011
KR    10-2013-0089037  8/2013

OTHER PUBLICATIONS

ISR dated Feb. 23, 2015 in PCT/KR2014/012761 published as WO 2015/099427.

*Primary Examiner* — Siamak Harandi
(74) *Attorney, Agent, or Firm* — Harness, Dickey & Pierce, P.L.C.

(57) ABSTRACT

The present disclosure relates to a method for generating an insertion trajectory of a surgical needle from an entry point to a target, including the steps of: preparing a medical image including the target and an anatomical structure; and extracting an insertion trajectory in consideration of at least one of a degree of invasion into the anatomical structure through the insertion trajectory and a distance of the insertion trajectory. Further, the present disclosure relates to a method
(Continued)

for generating an insertion trajectory of a medical device, and a robot for interventional procedures including needle insertion.

9 Claims, 35 Drawing Sheets

(51) Int. Cl.

| | |
|---|---|
| *A61B 10/02* | (2006.01) |
| *A61B 17/34* | (2006.01) |
| *A61B 34/30* | (2016.01) |
| *A61N 1/05* | (2006.01) |
| *A61N 1/372* | (2006.01) |
| *G06K 9/62* | (2006.01) |
| *G06T 7/00* | (2017.01) |
| *G06T 15/06* | (2011.01) |
| *G06F 19/00* | (2018.01) |
| *G06T 17/00* | (2006.01) |
| *G06T 19/20* | (2011.01) |
| *G06T 7/12* | (2017.01) |
| *A61B 34/37* | (2016.01) |
| *A61B 90/00* | (2016.01) |

(52) U.S. Cl.
CPC .......... *A61B 17/3403* (2013.01); *A61B 34/30* (2016.02); *A61B 34/37* (2016.02); *A61N 1/05* (2013.01); *A61N 1/0534* (2013.01); *A61N 1/372* (2013.01); *G06F 19/00* (2013.01); *G06K 9/6282* (2013.01); *G06T 7/0014* (2013.01); *G06T 7/12* (2017.01); *G06T 15/06* (2013.01); *G06T 17/005* (2013.01); *G06T 19/20* (2013.01); *A61B 2034/107* (2016.02); *A61B 2034/305* (2016.02); *A61B 2090/0801* (2016.02); *G06T 2207/20112* (2013.01); *G06T 2207/30061* (2013.01); *G06T 2207/30101* (2013.01); *G06T 2219/2021* (2013.01)

(58) Field of Classification Search
CPC ...... A61B 2034/305; A61B 2090/0801; A61B 34/10; A61B 34/30; A61B 34/37; A61B 6/03; G06K 9/6282
See application file for complete search history.

(56) References Cited

U.S. PATENT DOCUMENTS

| | | | |
|---|---|---|---|
| 2007/0049861 A1 | 3/2007 | Gundel | 604/27 |
| 2012/0184844 A1 | 7/2012 | Gielen et al. | 600/424 |
| 2012/0330325 A1 | 12/2012 | Devengenzo et al. | 606/130 |
| 2013/0197355 A1 | 8/2013 | Lee et al. | 600/424 |

(a) Distance field generation using an octree (b) Initial boundary surface (left) and inner surface extraction (right)

Overall procedure for vessel classification (a)

(b)

(a)

(b)

METHOD FOR GENERATING INSERTION TRAJECTORY OF SURGICAL NEEDLE

CROSS-REFERENCE TO RELATED APPLICATIONS

This application is a national phase application of PCT Application No. PCT/KR2014/012761, filed on 23 Dec. 2014, which claims benefit of Korean Patent Application Nos. 10-2013-0161288, 10-2013-0161284 and 10-2013-0161279, filed on 23 Dec. 2013. The entire disclosure of the applications identified in this paragraph are incorporated herein by reference.

FIELD

The present disclosure relates to a method for generating an insertion trajectory of a surgical needle, and more particularly, to a method for automatically generating an insertion trajectory of a surgical needle.

Further, the present disclosure relates to a method for generating an insertion trajectory of a medical device, and more particularly, to a method for automatically generating an insertion trajectory of a medical device.

Further, the present disclosure relates generally to a robot for interventional procedures including needle insertion, and more particularly, to a robot for interventional procedures including needle insertion, which is designed to reduce the fear of a patient experienced by a needle-type surgical tool.

BACKGROUND

This section provides background information related to the present disclosure which is not necessarily prior art.

Image-guided biopsy, which is an interventional procedure minimizing damage to surrounding normal healthy tissue and sampling for pathological diagnosis of neoplastic diseases, has found broad applications in sites including retroperitoneum of adrenal glands, pancreas, lymphatic glands or the like, lung mediastinum, spine, appendicular bones, etc. Image-guided biopsy enables detailed, three-dimensional localization of a lesion site using high-resolution medical images, and a visible biopsy needle entered a tissue facilitates the detection of small-sized lesions.

In a surgery site where image-guided biopsy is performed, an insertion trajectory of a biopsy needle can be guided by CT or C-arm fluoroscopy images. Due to the radiation exposure risks, however, it is customary to plan out the insertion trajectory beforehand from diagnostic images. For instance, an entry angle of the biopsy needle entering the body of a patient is important for planning an insertion trajectory, and the insertion trajectory is then planned after the entry angle and the entry point are determined. Meanwhile, this insertion trajectory plan is heavily dependent on experiences of the surgeon, rather than the objective bases on a degree of invasion into a vessel or bone. As such, each surgeon may select a different optimal insertion trajectory for a biopsy of the same lesion. In particular, for a lung biopsy using fluoroscopy, it is customary to select a shortest insertion trajectory from an axial 2D image. In a real surgery site, however, there is a big risk of hemorrhage or bleeding which often occurs during a biopsy procedure.

Advances in medical imaging technologies, in particular, X-RAY CT imaging make it possible to observe millimeter or smaller-sized microstructures in vivo. Technologies involved in spatial resolution as well as temporal resolution of images have also been developed over a short period of time. Nevertheless, a challenge still remains for finding an insertion trajectory without interfering with pulmonary vessels, mainly due to complicated morphology of the pulmonary vessels, e.g. a high density of the vessel distribution, close intersections, or the presence of other neighboring vessels running side by side. Therefore, it is necessary to provide more objective and quantitative bases on a degree of invasion into a vessel caused by an intended insertion trajectory as well as a distance of the insertion trajectory. Also, it would be very convenient and make great contributions to an increased safety level of surgery if there is a way to automatically generate a three-dimensional, minimally invasive and shortest insertion trajectory.

U.S. Pat. No. 6,487,431 discloses a technology of displaying multiple CT image slices in real time on a display monitor to guide a biopsy needle along the guideline indicated. However, this document does not present a method for objectively and quantitatively evaluating a degree of invasion by the guide line (insertion trajectory) itself for connecting an entry point to a target, and whether the guideline is indeed an optimal inversion trajectory.

When a medical device including a lead for deep brain stimulation, a biopsy needle, a probe or a catheter for example is inserted or implanted into an internal part of the body, such as, lung, brain or liver, it is crucial that none of vessels or important anatomical structures should be damaged or they should minimally invaded.

A brain surgery, for example, includes all neurosurgical operations that affect different functions of the brain. These neurosurgical operations cover not only tumor removal operations, but also deep brain stimulation (DBS) for stimulating a certain region in the brain that has a specific function. For instance, a neurosurgeon will perform DBS to treat serious diseases like Parkinson's disease, obsessive compulsive disorder and depression. In DBS, an electrode capable of suppressing or stimulating some portions of cerebral nerves needs to be implanted in a deep part of the brain in order to bring brain functions of a patient back to normal levels. The electrode may be arranged at the end of a lead, and the lead is then inserted along an insertion trajectory in the brain.

During the insertion of a medical device or during implantation, it is important to find an insertion trajectory for a lead, which would not damage any major structure including the cerebrovascular system, while bring a surgical tool such as a DBS electrode to a target in a very precise manner. An entry angle of the lead into the brain is a principle factor for planning an insertion trajectory. Once an entry angle and an entry point are determined, an insertion trajectory may be generated. In reality, however, a conventional insertion trajectory plan is heavily dependent on experiences of the surgeon, rather than the objective and quantitative bases on a degree of invasion into a vessel or an important anatomical structure of the brain. As such, even for the same patient, surgeons will probably find different insertion trajectories. U.S. Pat. Application No. 2012/0184844 discloses a method for generating multiple insertion trajectories in DBS, but still any specific method for evaluating a degree of invasion in a given insertion trajectory itself and for planning an insertion trajectory without interfering with vessels is not mentioned here.

For an interventional procedure where a medical device including a lead for deep brain stimulation, a biopsy needle, a probe or a catheter for example is inserted or implanted into an internal part of the body, such as, lung, brain or liver, it is important that the interventional procedure is performed without damaging vessels, or in a minimally invasive manner.

Image-guided biopsy, which is one of interventional procedures minimizing damage to surrounding normal healthy tissue and sampling for pathological diagnosis of neoplastic diseases, has found broad applications in sites including retroperitoneum of adrenal glands, pancreas, lymphatic glands or the like, lung mediastinum, spine, appendicular bones, etc.

Among interventional procedures including needle insertion as in a biopsy, minimally invasive surgery has been rapidly growing. Such an image-guided biopsy uses an insertion trajectory that is planned out beforehand from diagnostic images, due to the radiation exposure risks. However, in a surgery site, an insertion trajectory of a biopsy needle is still guided by CT or C-arm fluoroscopy images, and an insertion trajectory is still searched out by experienced surgeons who should perform a surgical operation under radiation exposure. Therefore, there is a need to develop a robot for interventional procedures including needle insertion, so as to resolve the radiation exposure risks of operators or surgeons as well as patients and to promote the accuracy of a surgical operation. The use of a robot for interventional procedures including needle insertion is expected to save time for a surgical operation, thereby reducing the radiation exposure of a patient, to reduce complications in a patient, and to maximize safety. Further, it is possible to get rid of the radiation exposure risks of a surgeon, and the surgeon can benefit from improved safety through such an automated system.

This interventional procedure like inserting a needle is typically performed as follows: the robot for an interventional procedure is set up, a biopsy needle is installed in the robot, the robot automatically moves and takes its place in an initial position in response to an external control signal, and the biopsy needle is then shifted right in front of an entry point on the skin of a patient.

In the meantime, some patients get afraid or feel inconvenient of using the biopsy needle. Moreover, an operator or assistant nearby may get stung by the biopsy needle and become infected, or the biopsy needle can collide with other equipment and become infected itself.

U.S. Pat. Application No. 2012/0330325 discloses a robot equipped with a biopsy needle which is being exposed as is. The document has neither acknowledged the problems thereof, nor suggested or implied any way to resolve the problems.

DISCLOSURE

Technical Problem

The problems to be solved by the present disclosure will be described in the latter part of the best mode for carrying out the invention.

Technical Solution

This section provides a general summary of the disclosure and is not a comprehensive disclosure of its full scope or all of its features.

According to an aspect of the present disclosure, there is provided a method for generating an insertion trajectory of a surgical needle, including the steps of: preparing a medical image including a target and an anatomical structure; and extracting an insertion trajectory in consideration of at least one of the following: a degree of invasion into the anatomical structure through the insertion trajectory, and a distance of the insertion trajectory.

According to an aspect of the present disclosure, there is provided a method for generating an insertion trajectory of a medical device starting from an entry point to a target, comprising the steps of: preparing an image of a surgical target image including the target and an invasion prohibited region; designating an initial entry region including an insertion trajectory, in which the initial entry region has a 3D truncated column having a progressively diminishing cross-section towards the target; deciding whether the initial entry region and the invasion prohibited region intersect each other; and generating a safe entry region by diminishing the initial entry region to avoid an intersection.

According to an aspect of the present disclosure, there is provided a robot for interventional procedures including needle insertion, including: a robot arm to be positioned near a patient, in response to an externally applied control signal; a needle-type surgical tool to be carried by the robot arm; and a protection module installed at the robot arm and adapted to cover up the needle-type surgical tool from sight of the patient.

Advantageous Effects

The advantageous effects of the present disclosure will be described in the latter part of the best mode for carrying out the invention.

DESCRIPTION OF DRAWINGS

FIG. 9 is actually implemented.

BEST MODE FOR CARRYING OUT INVENTION

Hereinafter, the present disclosure will now be described in detail with reference to the accompanying drawings. The detailed description of exemplary embodiments herein makes reference to the accompanying drawings, which show exemplary embodiments by way of illustration. While these exemplary embodiments are described in sufficient detail to enable those skilled in the art to practice the inventions, it should be understood that other embodiments may be realized and that logical changes and adaptations in design and construction may be made in accordance with this invention and the teachings herein. Thus, the detailed description herein is presented for purposes of illustration only and not of limitation. The scope of the invention is defined by the appended claims. For example, the steps recited in any of the method or process descriptions may be executed in any order and are not necessarily limited to the order presented. Furthermore, any reference to singular includes plural embodiments, and any reference to more than one component or step may include a singular embodiment or step.

Figure 1:
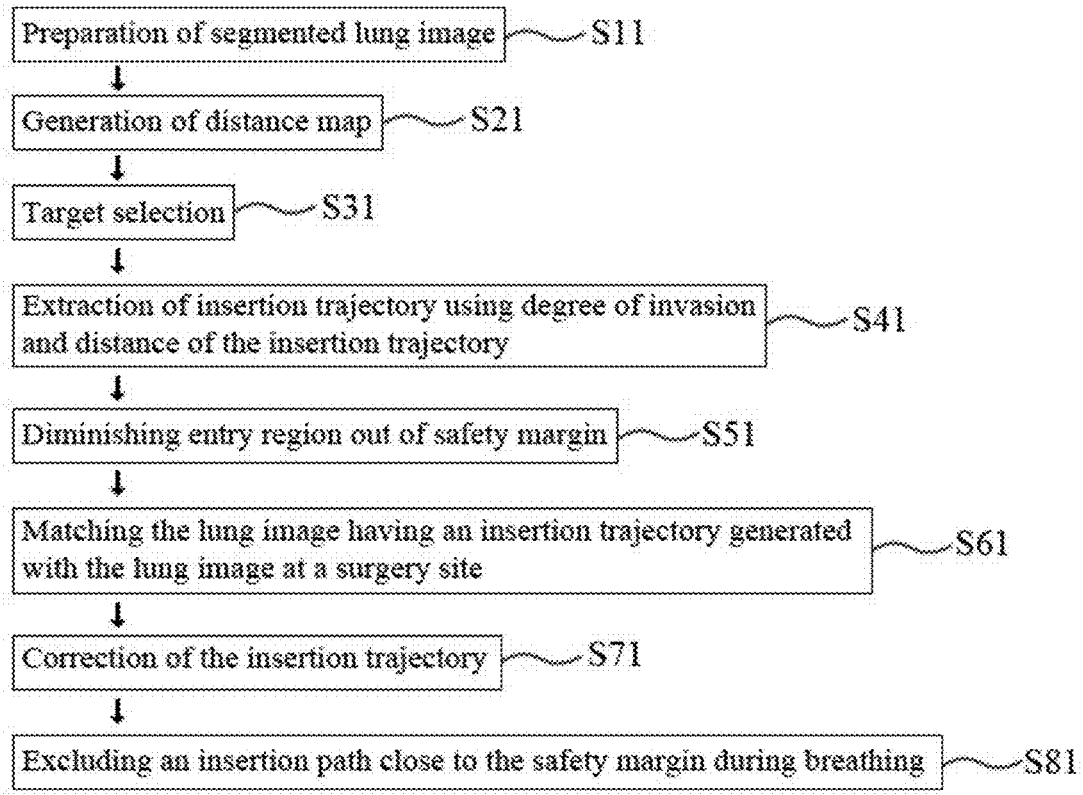
FIG. 1 describes one exemplary embodiment of a method for generating an insertion trajectory of a surgical needle according to the present disclosure.

FIG. 1 describes one exemplary embodiment of a method for generating an insertion trajectory of a surgical needle according to the present disclosure.

In the method for generating an insertion trajectory of a surgical needle, in a medical image including a target is first prepared (S11). Then, an entry point of the surgical needle is decided from the medical image, and an insertion trajectory is selected in consideration of at least one of the following: a degree of invasion through the insertion trajectory from the entry point to the target 100 (see FIG. 6), and a distance of the insertion trajectory (S41).

The medical image can be prepared by processing a basic medical image (e.g. segmentation) acquired from a medical imaging apparatus. Once the segmentation process is performed, an anatomical structure (e.g., vessel, bone, etc.) included in the medical image may be provided as a 3D set of voxels. A distance map can be generated using the set of voxels (S21), and a target of the surgical needle can be selected from the segmented medical image (S31). In order to extract an insertion trajectory, a weighing value is applied to a distance of the insertion trajectory from the entry point to the target, and weighing values (weights) are applied to each distance from the insertion trajectory to an anatomical structure included in the medical image, i.e. a degree of invasion, and these are summed up to generate at least one insertion trajectory within an allowable limit (S31). Those extracted insertion trajectories may form a conical entry region, and the entry region may be reduced, taking account of a safety margin (S51). The insertion trajectory thus obtained is then inputted into the medical image for surgical planning. In a surgery site, an image of the surgery site is taken and matched with the planning image, and an insertion trajectory is marked on the image of the surgery site, so as to guide a surgical operation (S61). This insertion trajectory may be corrected using a user interface (S71), and any inappropriate insertion trajectory in view of breathing or a movement may be removed (S81).

Each process will now be explained in further detail below.

Figure 2:
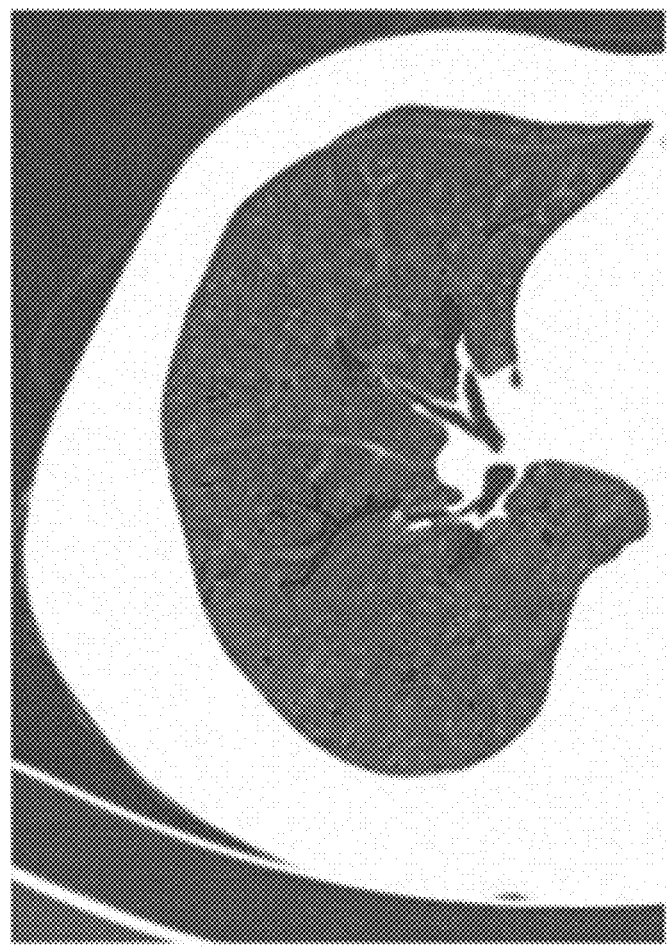
FIG. 2 shows an example of a segmented lung image.

FIG. 2 shows an example of a segmented lung image.

While the method for generating an insertion trajectory of a surgical needle may be applied to organs such as lung, kidney, liver, and so on, it can also be applied to other sites besides the organs. The following description is given with respect to the lung as a representative example.

A volumetric chest CT image (hereinafter, lung image) is obtained, and the lung image is then segmented to prepare a segmented lung image (S11). For instance, an anatomical structure (e.g., vessel, rib, airway or lung boundaries, etc.) included in the lung image is segmented by a segmentation technique (e.g., adaptive threshold). As a result of the segmentation, the anatomical structure like a vessel is extracted as a 3D set of voxels (e.g., see the segmented vessel illustrated in the first picture on the left side in FIG. 4). In particular, FIG. 2 shows an axial cross-section of the lung image, with the anatomical structure such as a vessel being segmented. The anatomical structure such as vessel, rib, airway or the like segmented from the lung image can be saved in a lung mask, a vessel mask, a rib mask, or an airway mask.

Figure 3:
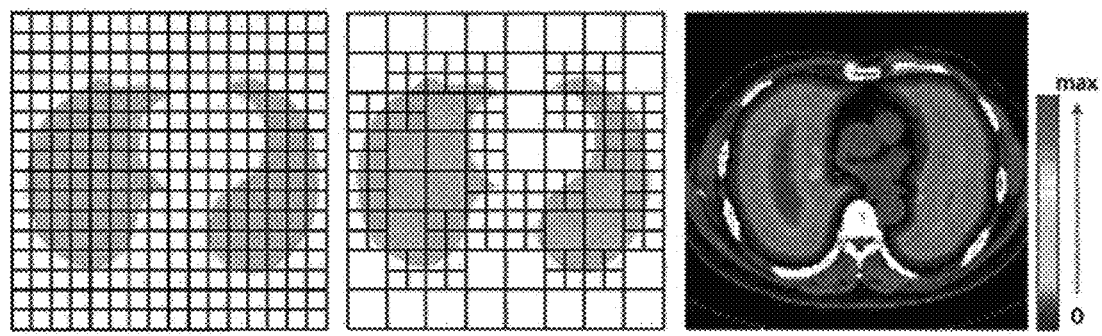
FIG. 3 shows an example of a method for generating a distance map.
Figure 3:
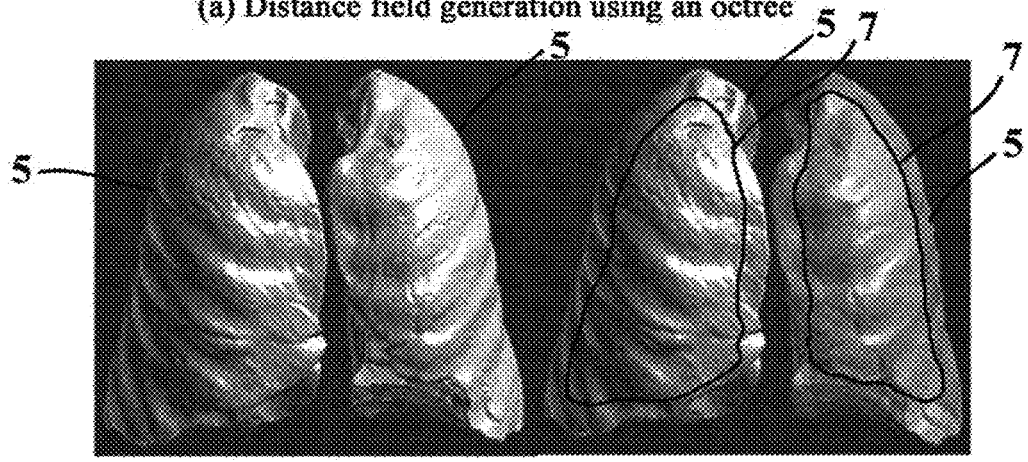

FIG. 3 shows an example of a method for generating a distance map.

Here, a distance map of lung boundary, a distance map of rib, a distance map of pulmonary vessel, or a distance map of airway can be generated using the lung mask, the vessel mask, the rib mask, or the airway mask described above (S21).

For instance, a process of generating the distance map of a pulmonary vessel may involve providing every voxel in the lung image with distance data from the vessel boundary to each voxel. Likewise, a process of generating the distance map of lung boundary, the distance map of rib, and the distance map of airway involves providing voxels with data on the distance from the lung boundary, the distance from the rib boundary and the distance from the airway boundary. With these distance maps, a distance of an insertion trajectory, or a distance between an insertion trajectory and an anatomical structure may be calculated. In this manner, it is possible to find an anatomical structure that intersects with the insertion trajectory of a surgical needle.

FIG. 3(a) shows an example of a method for generating a Euclidean distance map. The right and left sides of the lung segmented from the set of voxels on the lung image can be expressed mathematically as sets of voxels, LR, LL $\subset \Gamma$, respectively. Here, the set of voxels of the lung, $\Gamma=\{c|c=(i, j, k), i=1, \ldots, nx, j=1, \ldots, ny, k=1, \ldots, nz\}$. For instance, a Euclidean distance map can be obtained from the boundaries 5 (see FIG. 3(b)) for those LR, LL, so as to generate the distance map of lung boundary. A person skilled art would understand that the distance map can be generated using other methods, besides the Euclidean distance map.

Reference numeral 7 will be described later.

Figure 4:
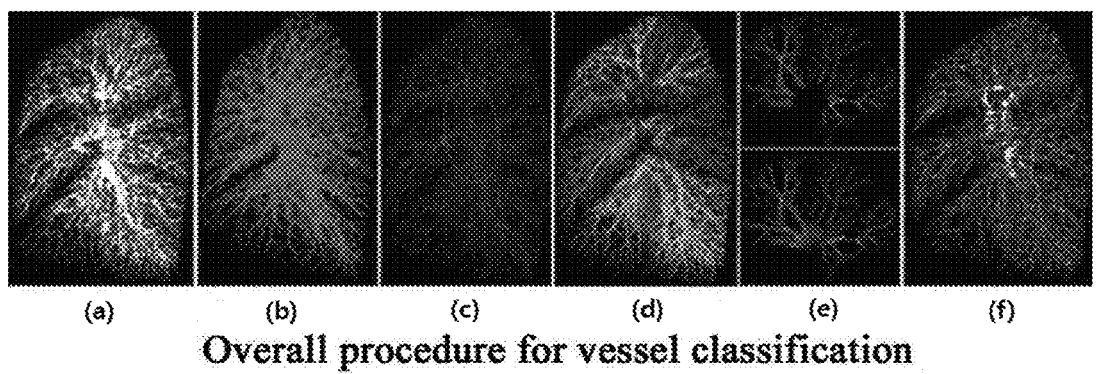
FIG. 4 shows an example of a method for constructing a pulmonary vessel tree.

FIG. 4 shows an example of a method for constructing a pulmonary vessel tree.

The aforementioned distance map may be used calculating a degree of invasion and a distance of an insertion trajectory to be described. Besides using the distance map, using a pulmonary vessel tree may also be taken into consideration, for calculating a degree of invasion and a distance of an insertion trajectory.

For instance, pulmonary vessel is extracted from volumetric chest CT images as a set of voxels (a point set extraction: FIG. 4(a)), and an initial pulmonary vessel tree is constructed using construction energy minimization (initial tree construction; FIG. 4(b)). Next, a mediastinal region is cut from the initial pulmonary vessel tree (cutting the proximal region; FIG. 4(c)), and branches of the initial pulmonary vessel tree are automatically segmented into sub-trees (automatically separated branches; FIG. 4(d)). Subsequently, the branches are extended to the mediastinal region cut from the branches of the initial pulmonary vessel tree, and sub-trees are merged (tree reconstruction and merging; FIG. 4(e)). Later, the pulmonary vessel is classified into pulmonary artery and pulmonary vein based on the reconstructed initial tree to construct a classified pulmonary vessel tree (artery and vein selection; FIG. 4(f)).

In the subsequent process, the number of vessels intersecting with the insertion trajectory and a degree of invasion into the vessels through the insertion trajectory are calculated, using the classified pulmonary vessel.

Generating an insertion trajectory is normally performed on a diagnosis image. In case of constructing a pulmonary vessel tree as described above, a process of distinguishing the pulmonary artery and the pulmonary vein is even performed on the diagnostic image, as this can be useful in the subsequence process. For instance, although it is important to distinguish the pulmonary artery and the pulmonary vein because a patient could die if air enters the pulmonary vein, it is hard to distinguish them in an actual surgical image. Therefore, segmentation of the pulmonary vessel is basically performed, but it is also possible that segmentation data on the artery and the vein on the diagnostic image are prepared and overlaid to be used for the surgical image. FIG. 4(f) is a sagittal view of the segmented pulmonary tree, and the pulmonary artery and the pulmonary vein are indicated by different colors for distinguishing between them (this color distinguishment is not indicated in FIG. 4(f)).

It is not absolutely required to use the pulmonary vessel tree, but the distance maps may be used as described above, to obtain a degree of invasion and a distance of an insertion trajectory. It is preferred to use the pulmonary vessel tree to get better accuracy in calculation of an insertion trajectory as well as a vessel intersection.

A method for constructing a classified pulmonary vessel tree as shown in FIG. 4 will now be explained with an equation.

First of all, the right side lung and the left side lung are segmented accurately into LR, LL $\subset \Gamma$ as a set of voxels, before the vessel is obtained as a set of voxels. Here, suppose that $\Gamma=\{c|c=(i, j, k), i=1, \ldots, nx, j=1, \ldots, ny, k=1, \ldots, nz\}$, a set of voxels of the lung image composed from CT scans, and I(c) represents an attenuation intensity of the voxel c. Vascular points $V=\{v_i\} \subset R^3$ are extracted first. Here, $v(c)=(x, y, z)^T=((c_i-0.5)\times dx, (c_j-0.5)\times dy, (c_k-0.5)\times dz)^T$, the central position of a corresponding voxel c. Other voxels of different types can also be classified by constructing an initial tree T=(V, E). Here, E represents a set of edges. The initial tree is constructed by minimizing the cost defined by Equation (1) below.

$$\min_T C(T) = \min_E \sum_{(i,j) \in E} C(i, j) = \min_E \sum_{(i,j) \in E} \frac{\|v_j - v_i\|}{\alpha + \beta \omega_j + \gamma e_{ij}} \quad (1)$$

where $w_j$ is a weighing value of the vertex j, $e_{ij}$ is a directional weighing value of the edge (i, j), and $\alpha, \beta, \gamma \in R$ are positive user-defined constants. $w_j$ is a value indicating the connection properties of vertex j, and defined as follows:

$$w_j = I(vj) + |\Phi(vj)| + \min\{1, 1 - \nabla^2 \Phi(vj)\}$$

where $I(v_j)$ is an attenuation intensity of the standardized $v_j$ by all vascular points, and $\Phi(v_j)$ is a standardized distance from the blood boundaries. $e_{ij}$ is a component that exhibits a directional similarity between the edge direction and the vascular orientation evaluated in $v_j$. A solution for minimizing Equation (1) will naturally become a minimum spanning tree (MST).

After constructing the initial tree, the mediastinal region is cut. Branches are separated from each other by grouping only those connected vertices, such that sub-trees are automatically formed.

Suppose $T_i=(V_i, E_i) \subset T$, where T is the i-th sub-tree. Before cutting, total optimization for minimizing the following Equation (2) derived from the article (Livny et al, "Automatic reconstruction of tree skeletal structures from point clouds", ACM Transactions on Graphics, vol. 29(6), Article 151, 2010) is carried out, and orientation vectors $\{o_i\}$ of all vertices are thus evaluated again.

$$\min_o \{\Delta E(T) + \Delta O(T)\} \quad (2)$$

$$\Delta E(T) = \sum_{v_i \in V} \left( w_i \left\| o_i - \frac{(V_i^P - v_i)}{\|V_i^P - v_i\|} \right\| \right)^2,$$

$$\Delta O(T) = \sum_{v_i \in V} \left( \frac{w_i^P + w_i}{2} \|o_P^i + o_i\| \right)^2$$

where $V_i^P$ is a parent vertex of vi. The groups are re-multiplied from each mediastinal vertex to a region with a cleaved end, using {oi}. If there are no overlapping branches, the groups are merged. Lastly, type of a vessel (artery or vein) is determined through a user interface based on the merged pulmonary vessel tree, and classified pulmonary vessel trees are constructed accordingly. These classified pulmonary vessel trees are saved as vessel masks $T_A$ and $T_v$, respectively, for the next step.

Although optional, the pulmonary vessels are classified into artery and vein, which enables to determine the number and thickness of invaded vessels through the insertion trajectory as well as the identity of an invaded vessel (i.e. artery or vein) in the subsequent process.

Figure 5:
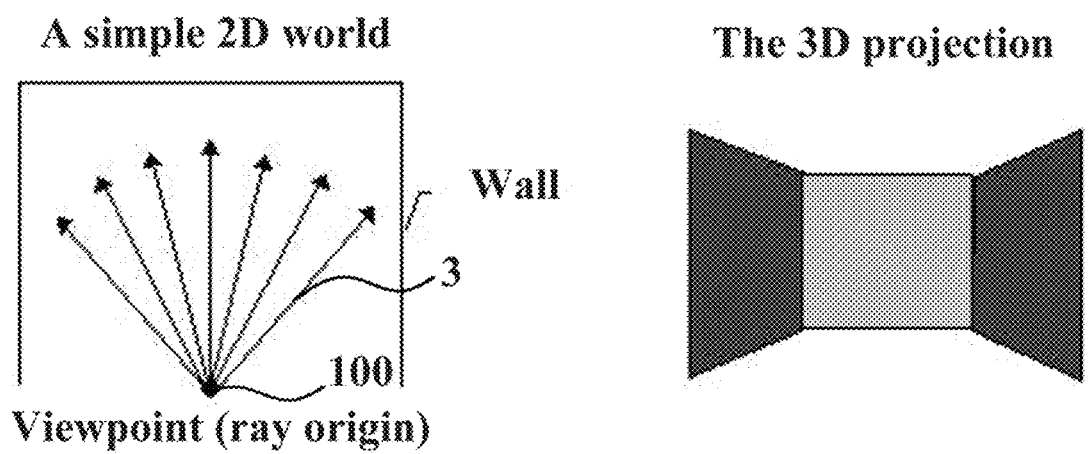
FIG. 5 shows an example of a ray casting method.

FIG. 5 shows an example of a ray casting method.

Locations of intersecting vessels can be found by tracing a projected ray 3 from a viewpoint (e.g. a target 100) with the ray casting method. In other words, it is possible to find voxels for vessels intersecting with the ray 3 at specific locations, or to obtain distances to the vessels.

For instance, a distance map of vessel includes distance data from the vessel boundary shown on the vessel mask to every voxel. Likewise, the number of vessels and the number of intersecting vessels within the ray trajectory can be obtained based on calculation results of every distance from the boundary of an anatomical structure beside the vessels using a mask thereof, i.e. using the distance maps described above.

Alternatively, a degree of invasion and a distance of an insertion trajectory may be obtained using the pulmonary vessel tree described above. As an example, one may find intersection points between the pulmonary vessel tree and an offset surface. For instance, the Euclidean distance map illustrated in FIG. 3(a) may be used to extract a virtual offset surface 7 arranged at the same distance from the pulmonary boundary 5 in form of a triangular mesh (see FIG. 3(b)). This triangular mesh can be calculated applying the well-known marching cubes algorithm, and the calculation process involved here may be done in a time-efficient manner by parallel computing using graphic processing units (GPUs). Then, it is possible to find which offset surface 7 has an intersection between the ray 3 and the vessel, for example. When a pulmonary vessel tree like the one described above is formed, basic components for a vessel is analyzed to obtain an orientation vector of the vessel. Meanwhile, the vessel in the classified pulmonary vessel tree does not always pass through the offset surface 7 vertically. Hence, in order to determine the diameter or area of the vessel, it is necessary to project the vessel onto the offset surface 7 vertically such that a cross-sectional offset area of the vessel on the offset surface may be calculated. Further, it is also possible to determine the radius of the vessel perpendicular to the orientation vector of the vessel using the offset area and the orientation vector of the vessel. Therefore, it is possible to get quantitative values including the number and thickness (or area) of vessels intersecting with the insertion trajectory.

Figure 6:
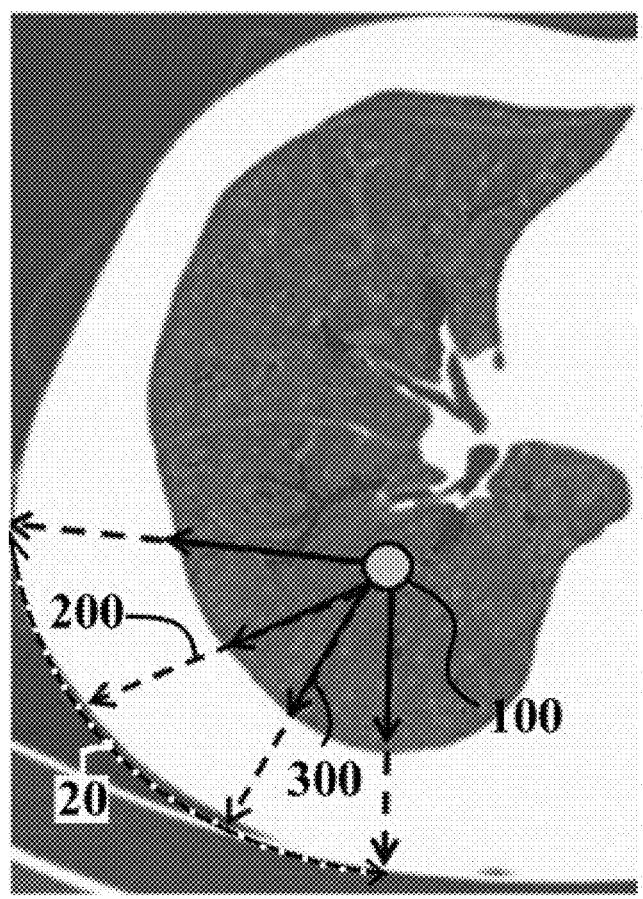
FIG. 6 shows an example of a method for extracting an insertion trajectory.

FIG. 6 shows an example of a method for extracting an insertion trajectory.

As described above, the distance to an anatomical structure, e.g. a vessel intersecting with the insertion trajectory may be determined by 3D ray casting, using either the distance map as illustrated in FIG. 5 or using the pulmonary vessel tree. The method for generating an insertion trajectory in 3D includes a method for extracting an insertion trajectory in 2D. The insertion trajectory in 3D goes beyond the limits of guiding the insertion trajectory on a 2D cross-section (e.g. axial cross-section). That is, an oblique insertion trajectory in 3D may be generated. In other words, the insertion trajectory in 3D may form an angle with two surfaces perpendicular to the axial section (sagittal view and coronal view). This means that more options are now available for optimizing an insertion trajectory.

First of all, a user (e.g., surgeon) can define an entry point range 20 to avoid unnecessary calculations, although an insertion trajectory may be found by ray casting for complete 360 degrees. The entry point range 20 may be set widely, except for a region where a surgical needle should not be inserted from medical perspectives. Once the entry point range 20 is decided, a computer sets an insertion trajectory from an entry point to a target by continuously trying different entry points within the entry point range 20 in an automated manner, and calculates a degree of invasion into a vessel for example and a distance of an insertion trajectory for each entry region. For instance, the entry point region 20 is given within a certain range, starting from the entry point of a shortest insertion trajectory 300, and then different entry points within the range are continuously tried until a degree of invasion and a distance of an insertion trajectory can be calculated. Although a 2D axial cross-section is illustrated in FIG. 6, it should be understood that an insertion trajectory may be extracted in 3D, as described previously. Here, the degree of invasion denotes the number and thickness (or area) of intersections between the insertion trajectory and an anatomical structure such as vessel. The distance of an insertion trajectory denotes the distance from the entry point of the pulmonary boundary to a target 100, for example. FIG. 5 and FIG. 6 illustrate how to obtain a degree of invasion or a distance of an insertion trajectory.

For instance, as expressed in the following equation, weighing values w1, w2, w3, w4 are applied to the distance Dlung from the entry point to the target 100, the distance Dairway from the insertion trajectory to the airway, the distance Dvessel from the insertion trajectory to the vessel, and the distance Drip from the insertion trajectory to the rip, respectively. These are then summed up to determine an angle ($\phi$) of the insertion trajectory. One example of the weighing values that can actually be applied can be w2, w4=10, w3=0.5, w1=0.5. These values mean that the insertion trajectory should never pass the airway and the rib, and the distance to the pulmonary boundary and the distance to the vessel can be treated equally.

$$\operatorname*{argmin}_{\phi} f(\phi) = w_1 \sum D_{lung} + w_2 \sum D_{airway} + w_3 \sum D_{vessel} + w_4 \sum D_{rib}$$

where $D_{rib} + \varphi < 0 \to D_{rib} = \infty$

Here, Drib can be infinite by a safety margin φ defined by the user. This implies that an insertion trajectory is not going to be generated as the insertion trajectory intersects with the rib. Therefore, an insertion trajectory of desirable conditions may be generated using each distance and each weighing value. In the above equation, Dlung of the insertion trajectory and the weighing value w1 are terms taken in consideration not the distance of the insertion trajectory, while Dairway (the distance to the airway from the insertion trajectory), Dvessel (the distance to the airway from the insertion trajectory), Dvessel (the distance to the vessel from the insertion trajectory), and the weighing values w2, w3, w4 are terms taken in consideration of a degree of invasion. For instance, if the weighing value, w1, for a distance of the insertion trajectory equals to 0, only the degree of invasion is considered such that an insertion trajectory 100 having a minimal degree of invasion can be extracted. Further, if the weighing values for the degree of invasion all equal to 0, an insertion trajectory 300 having a shortest distance can be extracted. An actual insertion trajectory may be determined by incorporating both approaches. For instance, a number of insertion trajectories having a degree of invasion within an allowable limit may be extracted, and then among those, an insertion trajectory having a shortest distance may be extracted.

Figure 7:
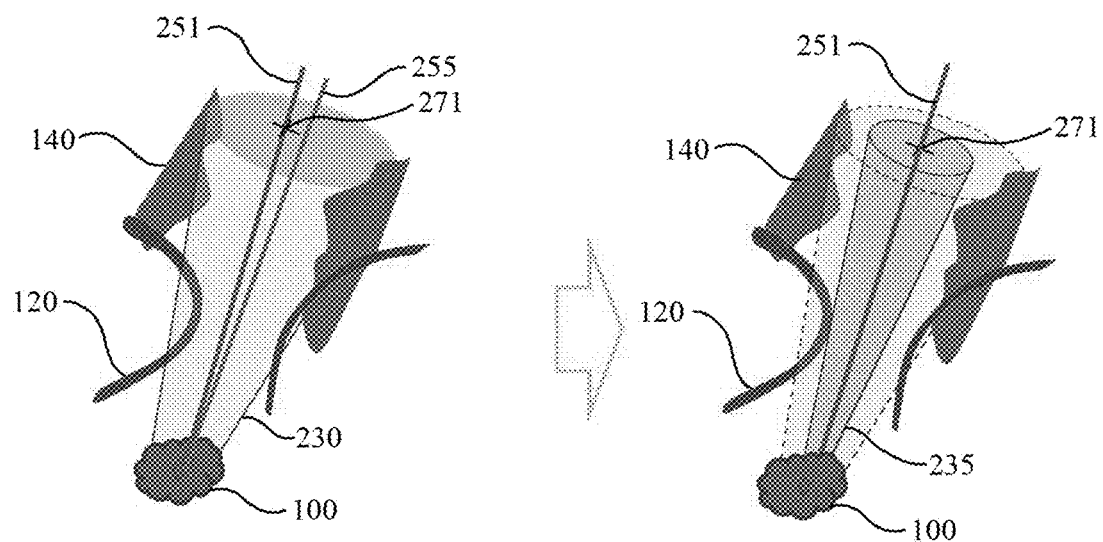
FIG. 7 shows a narrowed insertion trajectory outside a safety margin.

FIG. 7 shows a narrowed insertion trajectory outside a safety margin

It is possible to extract multiple insertion trajectories that satisfy the equation above. These multiple insertion trajectories can be marked in a roughly 3D entry region 230. The entry region 230 may have a cone shape having a progressively diminishing cross-section from an entry point 271 towards a target 100.

Empirically or theoretically, a safety margin can be determined for the entry region of a surgical needle. The safety margin can be an area at a certain distance away from a structure to be invaded, such as a vessel 140 or a virtual wall 120 (e.g., another organ besides lung). As such, in the entry region 230 which is a set of insertion trajectories generated by the equation above, those insertion trajectories within the safe region are preferably removed. Once the insertion trajectories within the safe region are removed, a narrowed entry region 235 will be generated.

Figure 8:
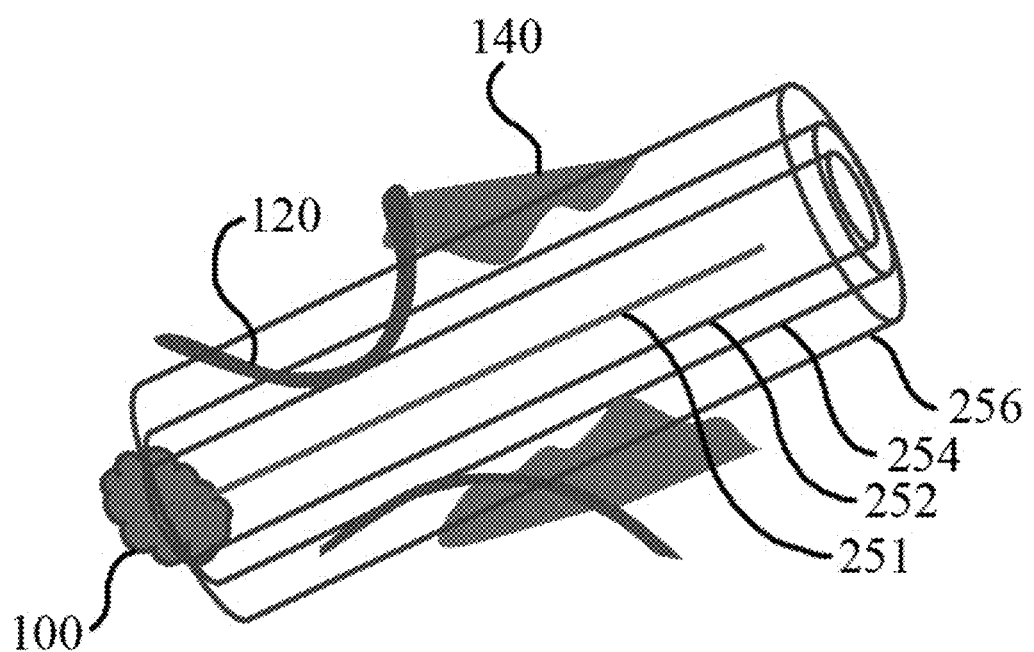
FIG. 8 shows different numbers of vessels according to size, which are located at a certain distance from a selected insertion trajectory.

FIG. 8 shows different numbers of vessels according to size, which are located at a certain distance from a selected insertion trajectory.

For instance, the central line in the narrowed entry region 235 can be primarily extracted as an insertion trajectory 251. Besides this insertion trajectory 251, another insertion trajectory can be selected within the range of the narrowed entry region 235. At least one insertion trajectory thus determined may be displayed on a pulmonary image with an insertion trajectory having been extracted, and the pulmonary image with an insertion trajectory being inputted becomes an image for surgical planning (see the left side picture in FIG. 11). This surgical planning image can be matched with a pulmonary image of a surgery site acquired from a patient in the surgery site. An insertion trajectory may be mapped and displayed on the matched pulmonary image of a surgery site (see the right side picture in FIG. 11). The surgeon may correct the insertion trajectory shown on the matched pulmonary image of a surgery site, using a user interface (e.g., mouse, etc.). Here, a degree of invasion by the corrected insertion trajectory and a distance of the insertion trajectory may be calculated and displayed on the matched pulmonary image or on another device. For instance, as shown in FIG. 8, it is possible to measure and display the number of vessels according to size, located on regularly spaced planes 252, 254, 256 with respect to the selected insertion trajectory 251. The display (e.g., the image of a surgery site) can show any indicator (e.g., the number of vessels according to size) that may be helpful for determining an insertion trajectory when the surgeon or operator adjusts or corrects the insertion trajectory.

Figure 9:
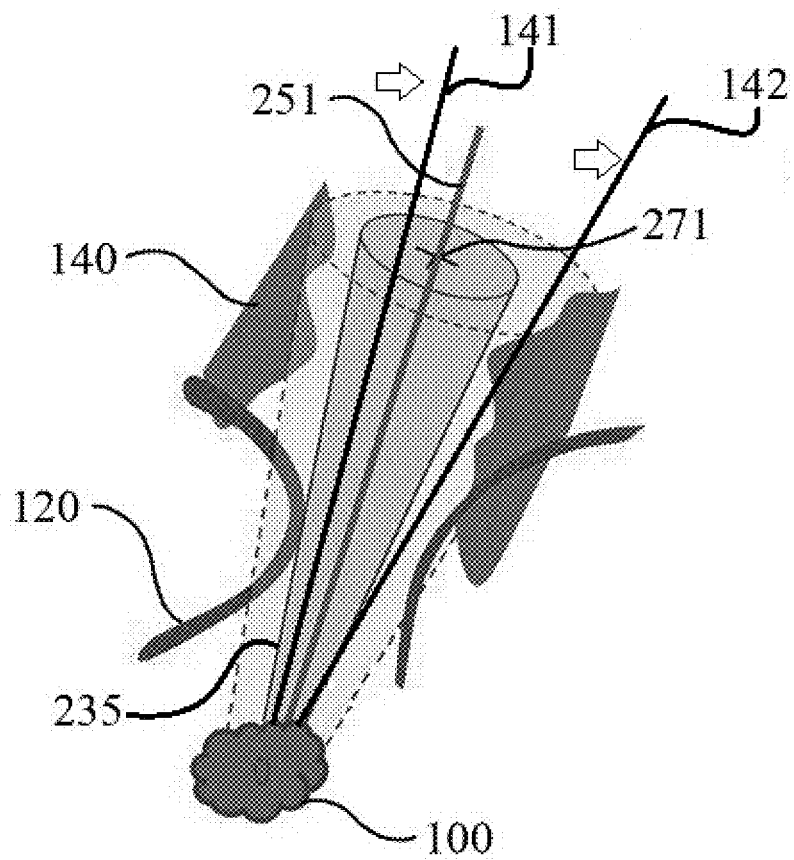
FIG. 9 shows a method for removing part of the insertion trajectory in consideration of a movement (e.g. breathing) detected in a surgery site.

FIG. 9 shows a method for removing part of the insertion trajectory in consideration of a movement (e.g., breathing) detected in a surgery site.

Meanwhile, since the image of a surgery site is a current image of a patient, there may be a movement caused by breathing of the patient. Therefore, the matched pulmonary image of a surgery site may include an insertion trajectory 142 being overlapped with a safety margin due to breathing, and an insertion trajectory 141 getting farther away from the safety margin. These can be found by observing a breathing cycle. Hence, it is preferable to remove the insertion trajectory 142 being overlapped with the safety margin due to breathing.

Figure 10:
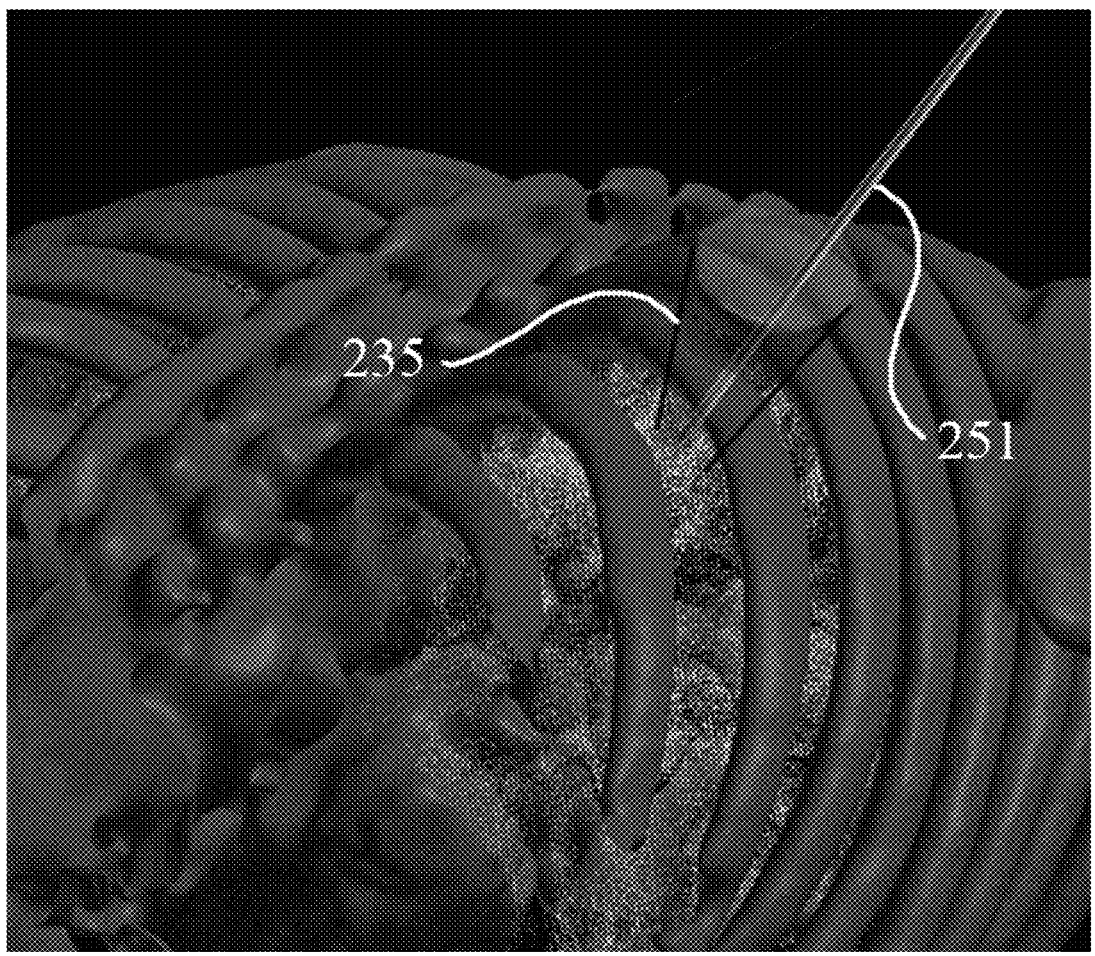
FIG. 10 shows an example where the insertion trajectory depicted in FIG. 8
Figure 11:
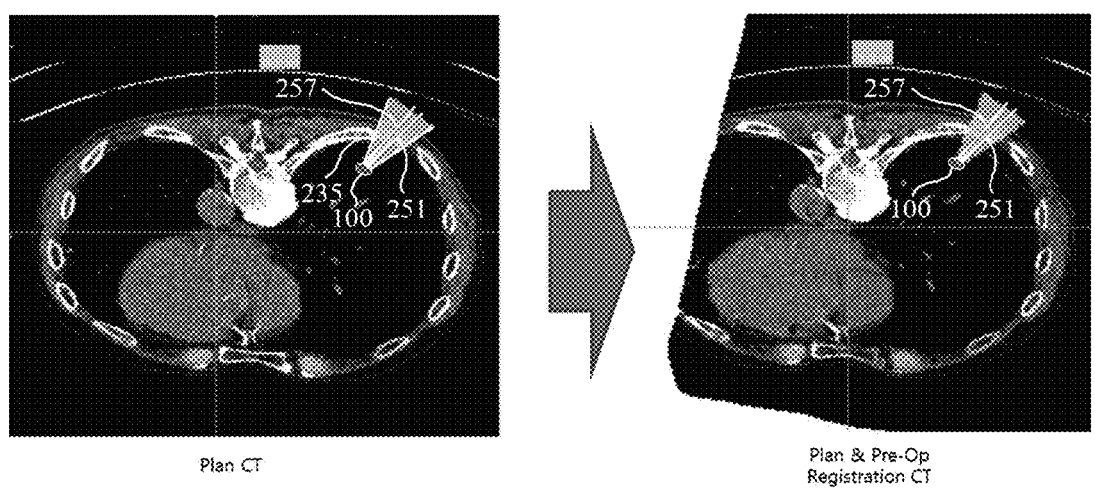
FIG. 11 shows an example of MPR images marked with the entry region and the optimal insertion trajectory depicted in FIG. 10.

FIG. 10 shows an example where the insertion trajectory depicted in FIG. 8 and FIG. 9 is actually implemented, and FIG. 11 shows an example of MPR images marked with the entry region and the optimal insertion trajectory depicted in FIG. 10.

Actual ribs, and a cone-shaped entry region 235 between the ribs, and an optimal insertion trajectory 251 may be three-dimensionally visualized, as shown in FIG. 10.

To confirm with certainty whether the entry region 235 and the optimal insertion trajectory 251 are three-dimensionally visualized, the entry region 235, the optimal insertion trajectory 251 and a user defined path 257 may be overlaid and displayed on the MPR (multiplanar reconstruction) (e.g., an axial view, a coronal view, a sagittal view) (FIG. 11 illustrates an axial view.).

As a surgical needle is guided along the confirmed insertion trajectory on the MPR, which is optimized for a degree of invasion, a distance of an insertion trajectory and even for breathing, any operation including a biopsy may be performed as required. For instance, a finally confirmed insertion trajectory may be transmitted to a robot or navigation equipment using TCP/IP or a dedicated communication protocol, and be advantageously used for an operation.

Figure 12:
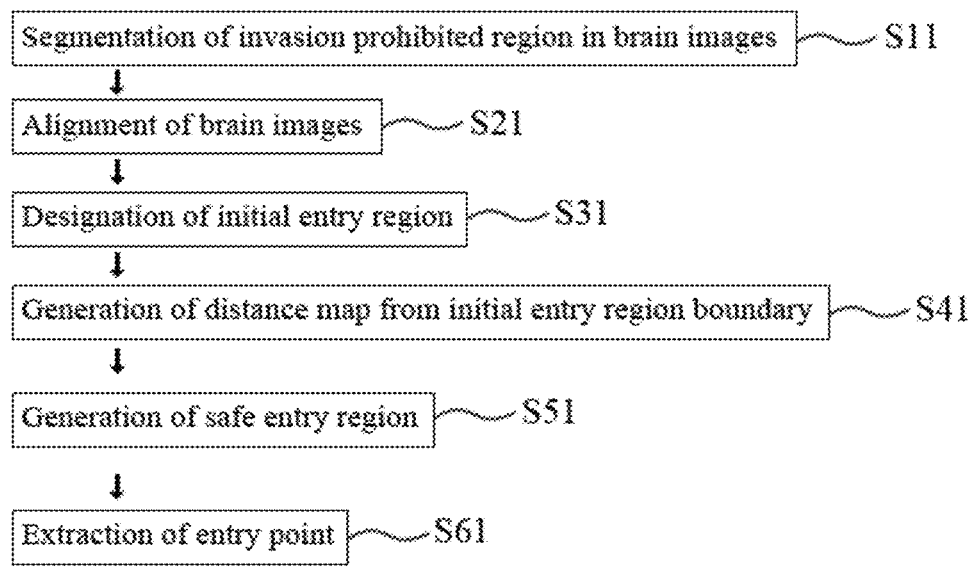
FIG. 12 describes an exemplary embodiment of a method for generating an insertion trajectory of a medical device according to the present disclosure.
Figure 13:
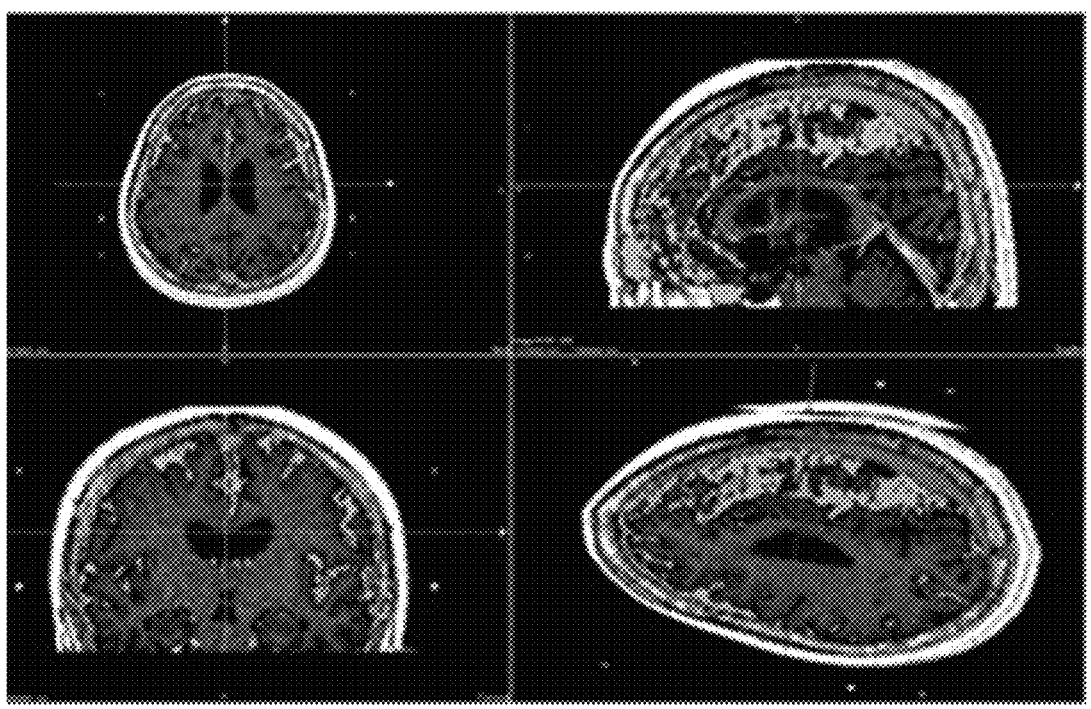
FIG. 13, FIG. 14, FIG. 15 and FIG. 16 show examples of a procedure for the preparation of brain images including a target and an invasion prohibited region.

FIG. 12 describes an exemplary embodiment of a method for generating an insertion trajectory of a medical device according to the present disclosure.

In the method for generating an insertion trajectory of a medical device, firstly, brain images including a target and an invasion prohibited region are prepared (S11). For instance, the brain images in a sagittal view, an axial view and a coronal view acquired from a medical imaging apparatus undergo the segmentation process and render an invasion prohibited region including a vessel and a target as a 3D set of voxels (S11), and these segmented brain images are subjected to volume alignment with respect to an anterior commissure-posterior commissure line (S21). Next, an initial entry region including an insertion trajectory is designated (S31). The initial entry region has a 3D column shape (e.g., a truncated column) having a progressively diminishing cross-section towards the target. For instance, the initial entry region is defined from the entry range to the target by designating an entry range onto the surface of the target shown on a target image. Following this, it is decided whether the initial entry region and the invasion prohibited region intersect each other. For instance, the distance from an initial entry region boundary to the invasion prohibited region is calculated using distance maps (S41). After that, a safe entry region with a diminished initial entry region to avoid intersections is generated (S51). An entry point may be extracted from the central line in the safe entry region (S61). As the insertion trajectory may be changed within the safe entry region, the safe entry region provides an allowable margin for the insertion trajectory. In other words, according to the method for generating an insertion trajectory of a medical device of the present disclosure, an entry region is extracted in form of 3D space, instead of individually extracting a single or multiple insertion trajectories. The method for generating an insertion trajectory of a medical device according to the present disclosure may be applied to diverse operations in which a medical device (e.g., a biopsy needle, a lead for DBS, a probe, a catheter, etc.) is urged to reach a target inside the body, and in particular, to an automated system for generating a non-invasive insertion trajectory in DBS. The following description will be given with respect to DBS as a representative example.

FIG. 13, FIG. 14, FIG. 15 and FIG. 16 show examples of a procedure for the preparation of brain images including a target and an invasion prohibited region.

Figure 14:
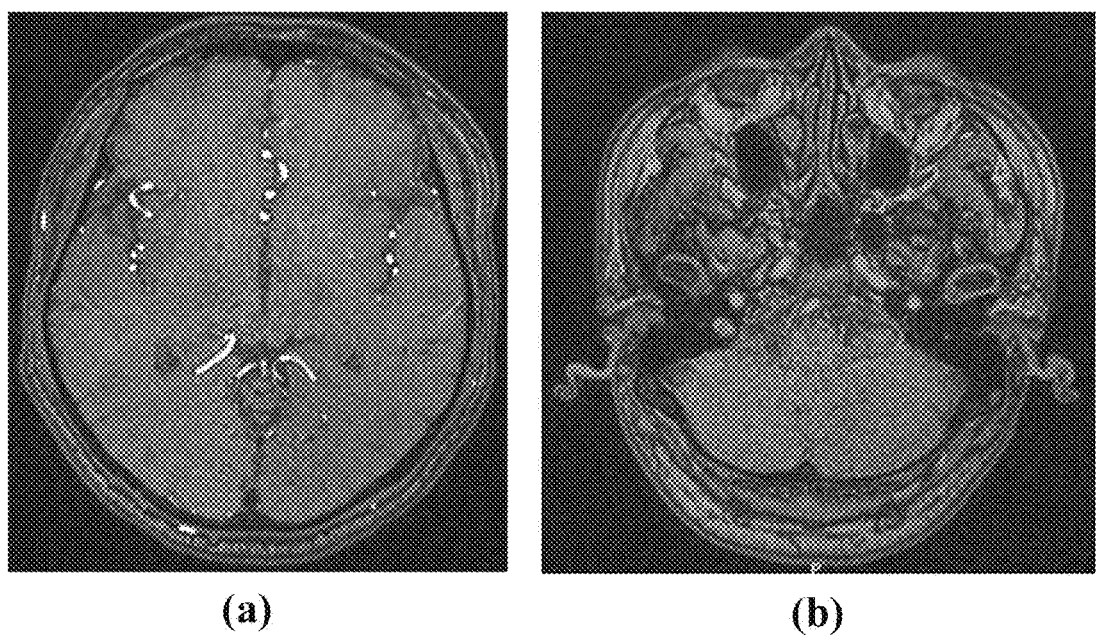
Figure 15:
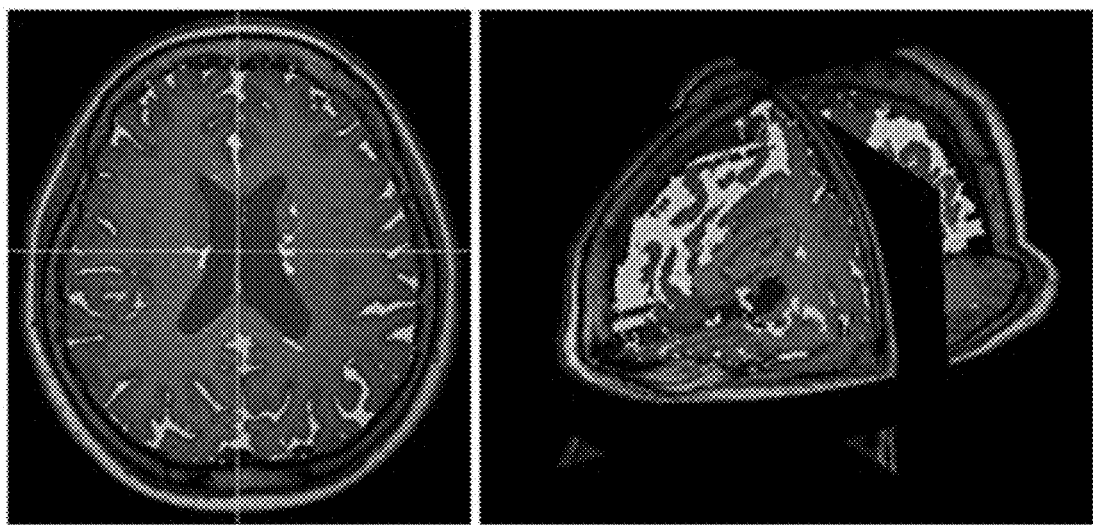
Figure 16:
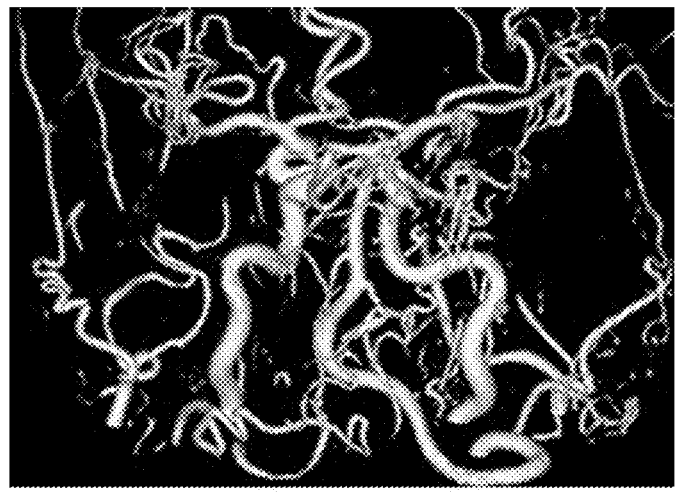
Figure 16:
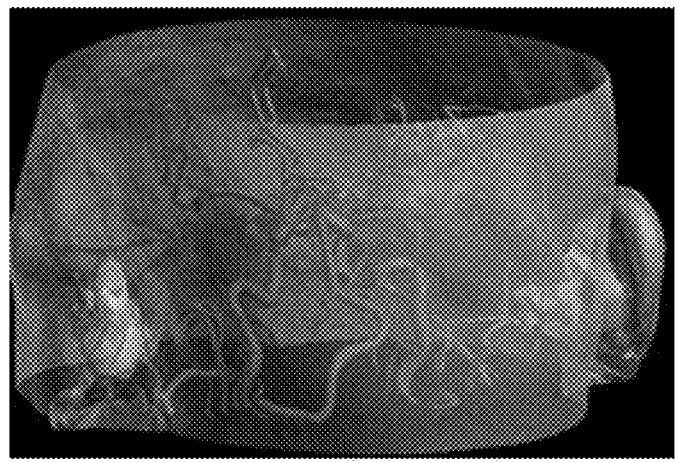

First of all, various MRI brain images (e.g., vessel angiography, T1, etc.) are created using MRI. The images are segmented into a target (see 100 in FIG. 20 and FIG. 22), and an invasion prohibited region (see 120, 140 in FIG. 22) (S11 in FIG. 12). For instance, on a T1 image, masks for regions that should not be damaged (invasion prohibited regions) including brain vessels, ventricle, etc., are generated, respectively, by software rending. It is also possible that a user determines the target. In the case of DBS, the target will be a part for performing a specific function of the brain, which becomes a target for stimulation. A DBS lead is provided with electrodes (e.g., 3 electrodes) for stimulating the target. Those brain images generated using MRI include brain images in a sagittal view (see the upper end on the right side), an axial view (see the upper end on the left side), and a coronal view (see the lower end on the left side). In the case of vessels, the vessels can be segmented as shown in FIG. 14 (b) by segmentation schemes (e.g., adaptive region growing) using an MRI brain angiography image in the axial view as shown in FIG. 14(a). Through this segmentation, the vessels such as artery and vein, and the invasion prohibited region such as ventricle, and the target may be obtained as a 3D set of voxels. Likewise, all safe regions except for those invasion prohibited regions may be obtained as a 3D set of voxels. Although the invasion prohibited regions and the safe regions are not distinguished by colors in FIG. 15, they may optionally be indicated by different colors. A 3D volume rendered (FIG. 16(a)) or 3D surface rendered (FIG. 16(b)) vascular structure may be constructed from the segmented vessels, using a medical imaging software.

Extracting an invasion prohibited region involves making an analysis based on the brain images provided and then saving the result in a mask. In the case of vessel, an invasion prohibited region is extracted by applying the segmentation process with a blood weighted image (thresholding, etc.) as described above. Meanwhile, a control program should be implemented using such mask information or the like, in order to prevent a surgical tool from entering the invasion prohibited region in the subsequent process. Although a mask larger than a voxel will suffice to accomplish the above at a desired level of accuracy, it is also optional to generate a surface model of the region and to apply an algorithm for finding intersections with a 3D modeled surgical tool, so as to obtain the desired level of accuracy with greater delicacy. In other words, mask intersections or 3D model intersections are obtained. Volume rendering and surface rendering are the techniques to visualize each data and show it to a person's eyes, as it needs to be confirmed by the person.

Figure 17:
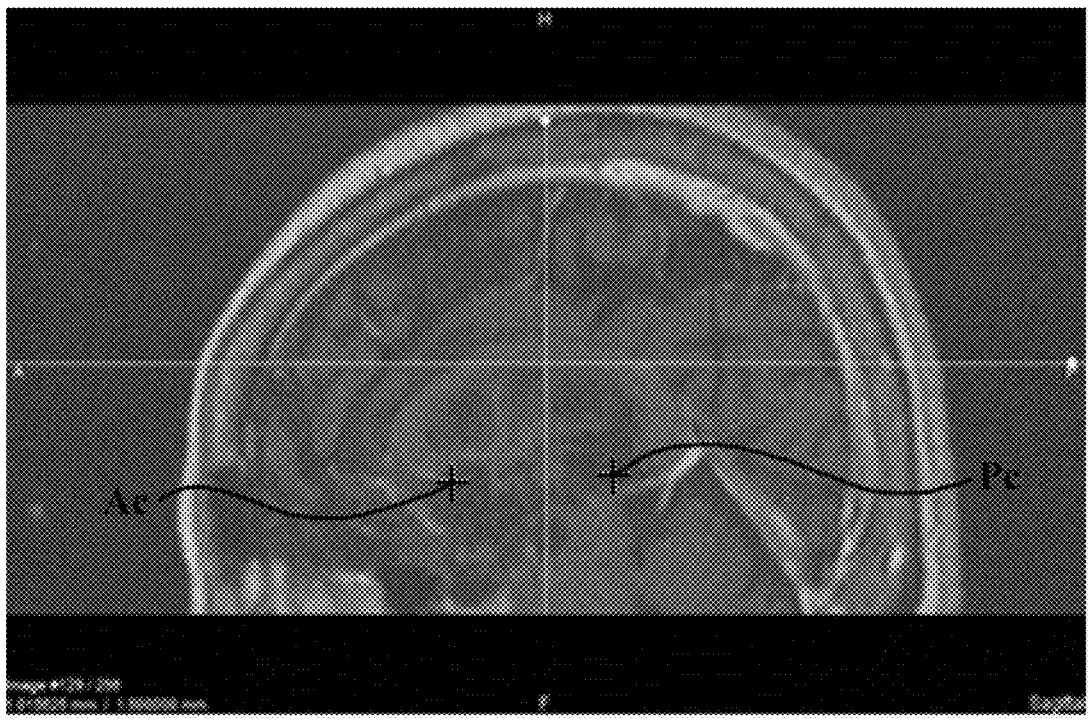
FIG. 17 and FIG. 18 show an example of volume-aligned brain images.
Figure 17:
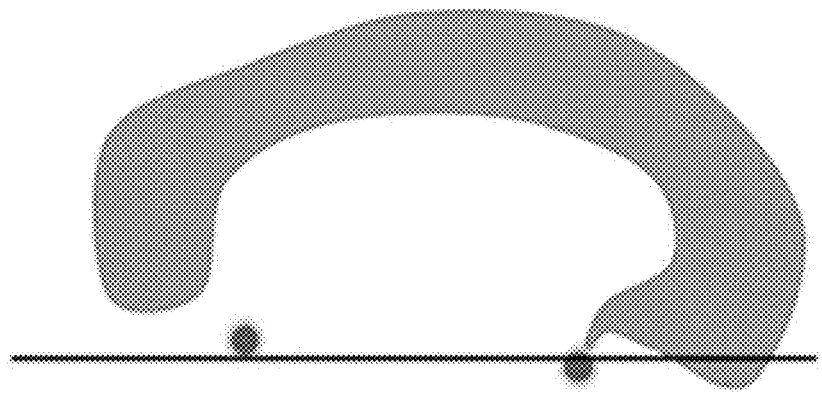
Figure 18:
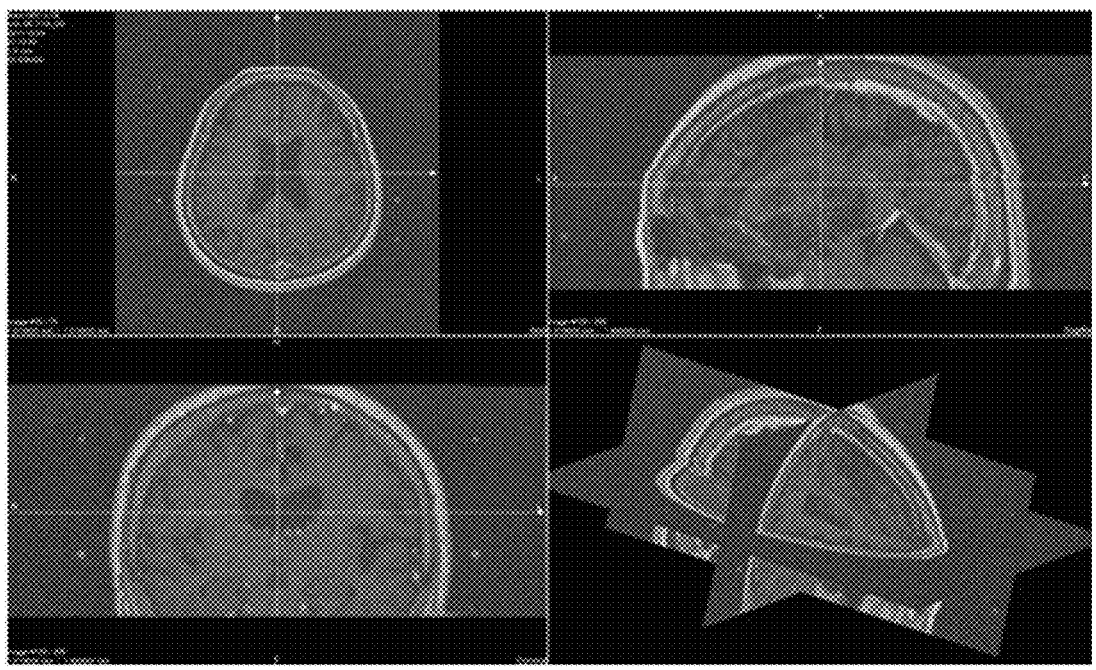

FIG. 17 and FIG. 18 show an example of volume-aligned brain images.

The segmented brain images are brought into volume-alignment with respect to an anterior commissure-posterior commissure line (AC-PC line) (S21 in FIG. 12).

For instance, a user is allowed to select two points AC and PC using a brain image in a sagittal view (see FIG. 7 and the upper end on the right side of FIG. 17) as well as two points AC and PC in the axial view (see the upper end on the left side of FIG. 18) and the coronal view (see the lower end on the right side). The sagittal view, the axial view and the coronal view are volume-aligned with respect to this AC-PC line (see the lower end on the right side of FIG. 18).

Figure 19:
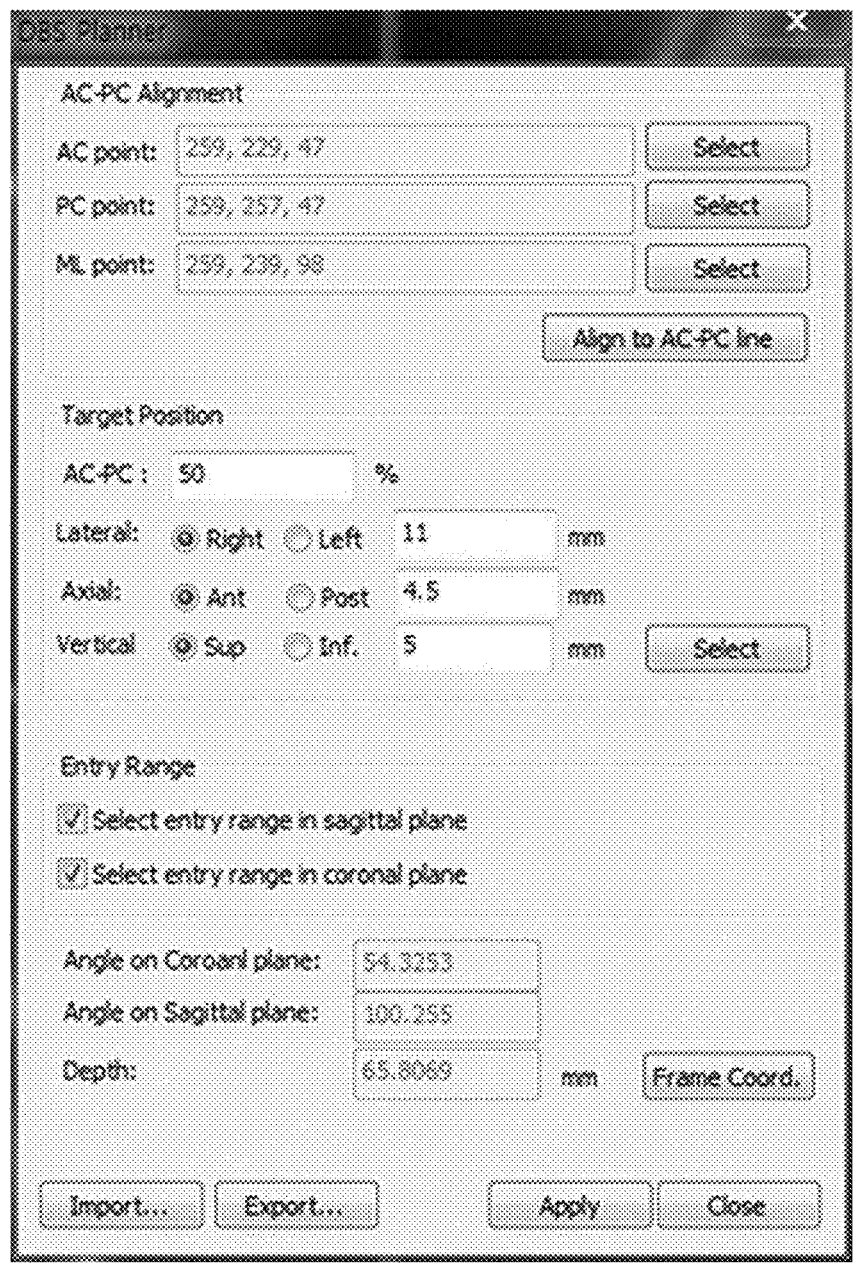
FIG. 19 shows an example of a software interface for planning an insertion trajectory.
Figure 20:
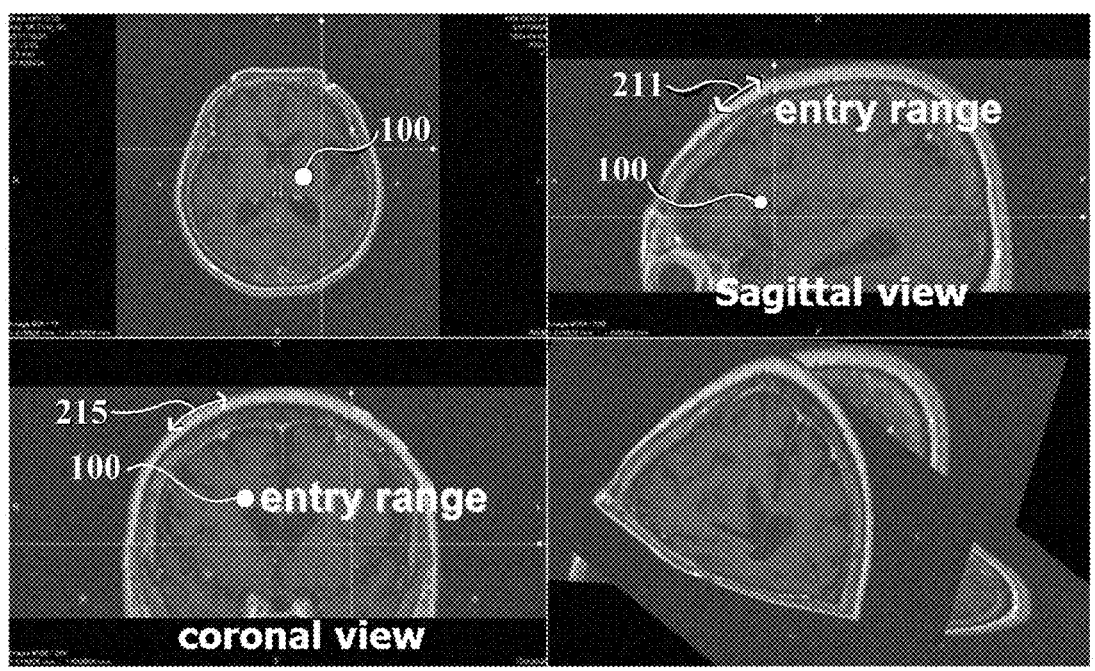
FIG. 20 shows an example of a method for designating an entry range.
Figure 21:
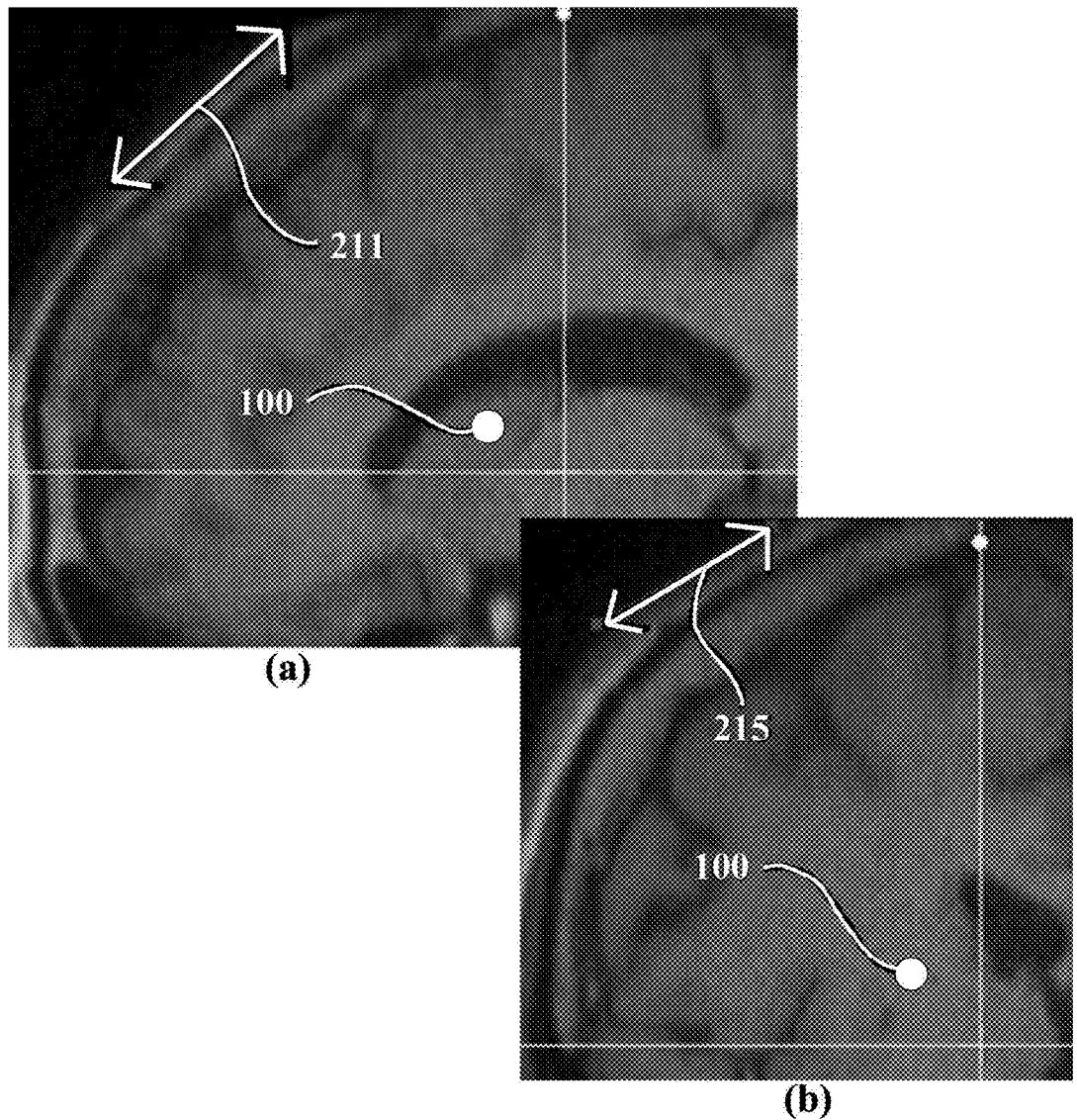
FIG. 21 is an enlarged view of a portion in FIG. 20.

FIG. 19 shows an example of a software interface for planning an insertion trajectory, FIG. 20 shows an example of a method for designating an entry range, and FIG. 21 is an enlarged view of a portion in FIG. 20.

A user designates an initial entry region (see 240 in FIG. 22(a)) (S31 in FIG. 12).

In this example, the insertion trajectory will eventually be extracted as a single line, but an allowable range for this final insertion trajectory is designated by a user. For instance, the allowable range for the insertion trajectory is designated as a certain region of a 3D column shape, being led to a target. This insertion trajectory designated by the user is defined as an initial insertion trajectory.

Referring to FIG. 19, the user is allowed to select data or values for AC-PC alignment, a target position, an entry range and so on through a software interface adapted to plan an insertion trajectory. Using this interface, for example, the user may designate each entry range 211, 215 in form of a line on the surface of the brain shown in the sagittal view (see the upper end on the right side of FIG. 20, and FIG. 21(a)) and the coronal view (see the lower end on the left side of FIG. 20, and FIG. 21(b)). Accordingly, the insertion trajectory that was designated by a line in each of the sagittal view and the coronal view orthogonal to each other can now be designated as a curved surface (see 210 in FIG. 22(b)) in a 3D volume.

Figure 22:
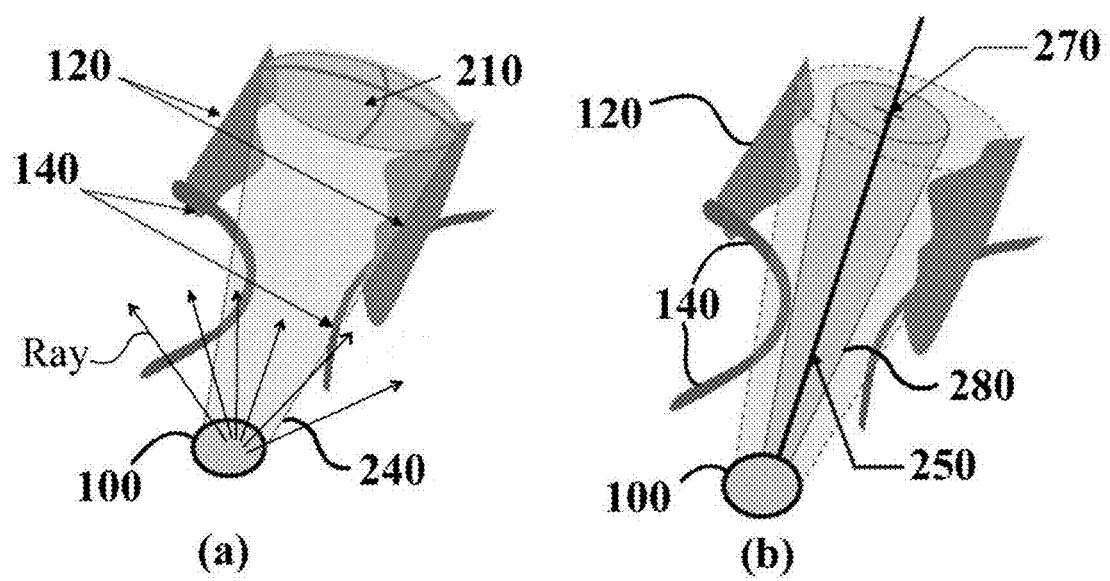
FIG. 22 shows an example of a procedure for generating a safe entry region from an initial entry region.

FIG. 22 shows an example of a procedure for generating a safe entry region from an initial entry region.

When the aforementioned entry range 210 is designated, an initial insertion trajectory 240 from the entry range 210 to a target 100 is defined as shown in FIG. 22(a). In this example, the initial entry region 240 has a truncated cone shape having a progressively diminishing cross-sectional towards the target 100. If the entry range 210 is not circular, a cone fitting process may be performed. As a result, the initial entry region 240 of the truncated cone shape is defined. Compared with the lung having a complicated vascular structure, the brain has a simpler vascular structure 140 including cerebral arteries and cerebral veins such that any experienced surgeon will be able to designate an initial entry region 240 running away from invasion prohibited regions 120, 140 including vessels. It is not an absolute requirement that the initial entry region 240 should completely avoid the invasion prohibited regions 120, 140. Rather, the initial entry region 240 may partially run across the invasion prohibited regions 120, 140 as a process of extracting a safe entry region 280 (to be described) will proceed (see FIG. 22(a)). In fact, the initial entry region 240 is simply intended to designate a smallest appropriate insertion trajectory for a subsequent process, and selected by a user based on his or her experiences and knowledge.

Next, it is decided whether the initial entry region 240 intersects with the invasion prohibited regions 120, 140. One way to do this is to calculate the distance from the boundary of the initial entry region to the invasion prohibited area. For instance, as shown in FIG. 22(a), a distance map from the boundary of the initial entry region 240 to the voxels of the invasion prohibited regions 120, 140 is generated by ray casting from the target 100 (S41 in FIG. 12).

This process of generating a distance map includes calculating the distance to the boundary plane for every voxel with respect to the boundary plane on a mask in the invasion prohibited region. Once the distance from the boundary plane of the invasion prohibited region such as a vessel, one can advantageously use the distance for computing a safe distance in real time when an insertion trajectory of a DBS lead is being generated or when a robot injects a surgical needle.

In addition, the distance map may be used to find voxels of the invasion prohibited regions 120, 140 such as a vessel located within the initial entry region 240. Moreover, it is also possible to obtain the distance between the boundary of the invasion prohibited regions 120, 140 and the boundary of the initial entry region 240. Going back to FIG. 22(*a*), one can see that the initial entry region 240, the vessel 140, and other important structures 120 of the brain (e.g., hippocampus, amygdala, etc.) partly intersect each other.

Then, as shown in FIG. 22(*b*), the initial entry region 240 is diminished to avoid the intersection, such that a safe entry region 280 is generated (S51 in FIG. 12). Whether or not the initial entry region 240 intersects with the invasion prohibited regions 120, 140, the initial entry region 240 is diminished anyway such that it is spaced a marginal distance away from the boundary of the invasion prohibited regions 120, 140 to ensure the safety involved. That is, the safe entry region 280 is a region included in the initial entry region 240. For instance, based on the distance map, the safe entry region 280 may be formed by diminishing the initial entry region 240 outside the safety marginal distance from the invasion prohibited regions 120, 140, and the safe entry region 280 may undergo a cone fitting process. The safe entry region 280 thus generated represents the range of an insertion trajectory that is applicable to an actual surgical operation. If the safe entry region 280 having been generated is too small or found to be inappropriate for some other reasons, another entry region may be designated, or a necessary procedure may be performed to obtain another safe entry region.

Figure 23:
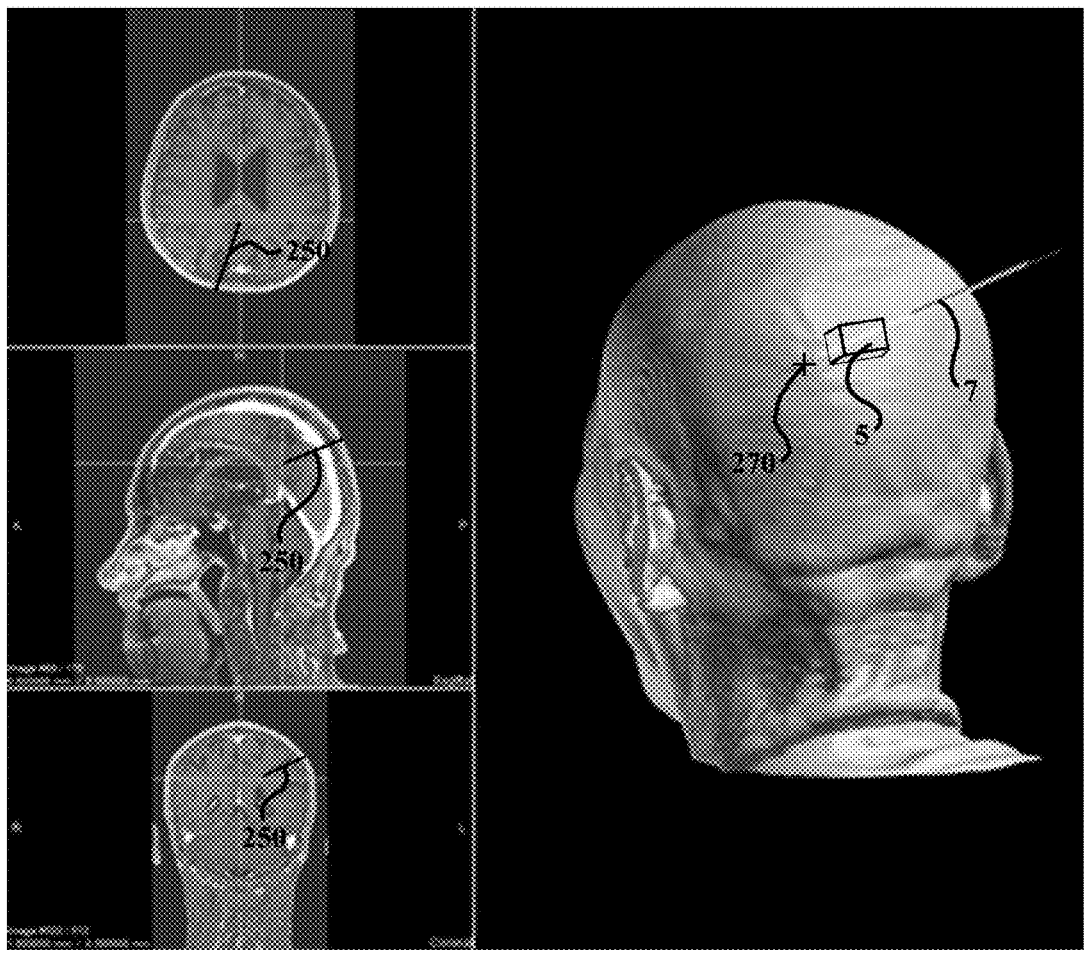
FIG. 23 shows an example of an insertion trajectory in sagittal, axial and coronal views, and in a 3D image.
Figure 24:
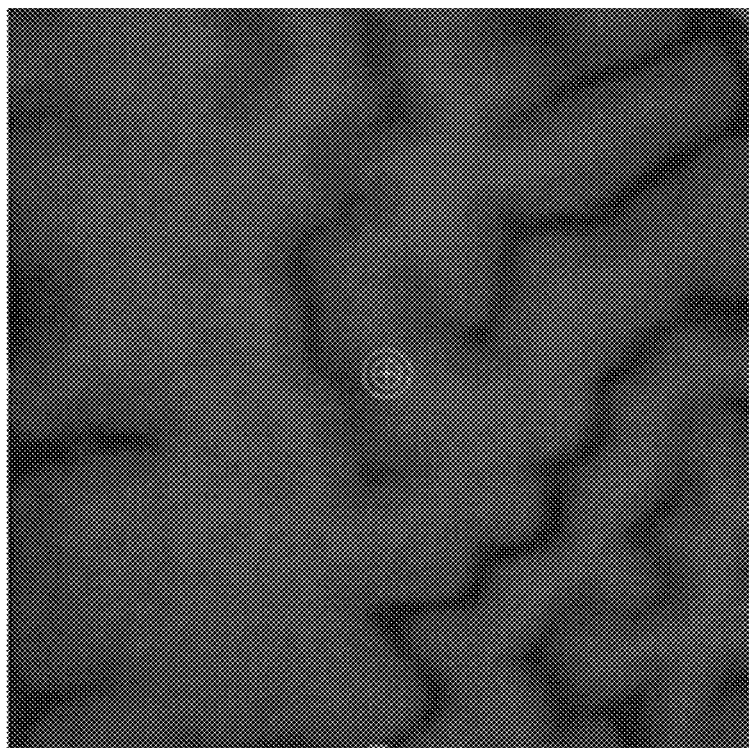
FIG. 24 shows an example of a brain image seen from the eyes of a surgeon.

FIG. 23 shows an example of an insertion trajectory in sagittal, axial and coronal views, and in a 3D image. FIG. 24 shows an example of a brain image seen from the eyes of a surgeon.

An intersection between the central line (see 250 in FIG. 22(*b*)) of the cone-shaped safe entry region 280 and the head surface shown on the brain images is extracted as an entry point 270 (see FIG. 22(*b*) and FIG. 23). An insertion trajectory is then extracted, starting from the entry point 270 to the target 100 (e.g., the center of the target). Any insertion trajectory within the safe entry region 280 can be suitable for being applied to all types of surgical operations, and it does not always have to follow the central line 250.

In this example, the method for generating an insertion trajectory of a medical device may include displaying brain images along the insertion trajectory. For instance, the brain images may be displayed as seen through a virtual camera 5 (e.g., 2D MPR image (projected path) or 3D surface view display) which is arranged at the medical device (e.g., DBS lead, 7), along the insertion trajectory from the entry point 270 to the target 100 (see FIG. 24). This view of the virtual camera 5 shows the brain images on which the medical device is going to pass along the insertion trajectory as seen through the surgeon's eye. Through this, the suitability of the insertion trajectory can be evaluated again, or corrected if necessary. The correction process can be simply done by directly inputting parameters for changing the path, or adjusting the entry point using a mouse, or shifting the insertion trajectory.

The aforementioned processes including designating the entry range 210, generating the initial entry region 240, generating a distance map, generating the safe entry region 280, extracting an insertion trajectory along the central line 250 and so on may be automated by means of a computer, under user-set conditions. Further, the brain images are used to evaluate objectively whether or not the medical device following the insertion trajectory has invaded the invasion prohibited regions 120, 140, and there is proposed a specific method for generating an injection trajectory running away from the invasion prohibited regions 120, 140.

Figure 25:
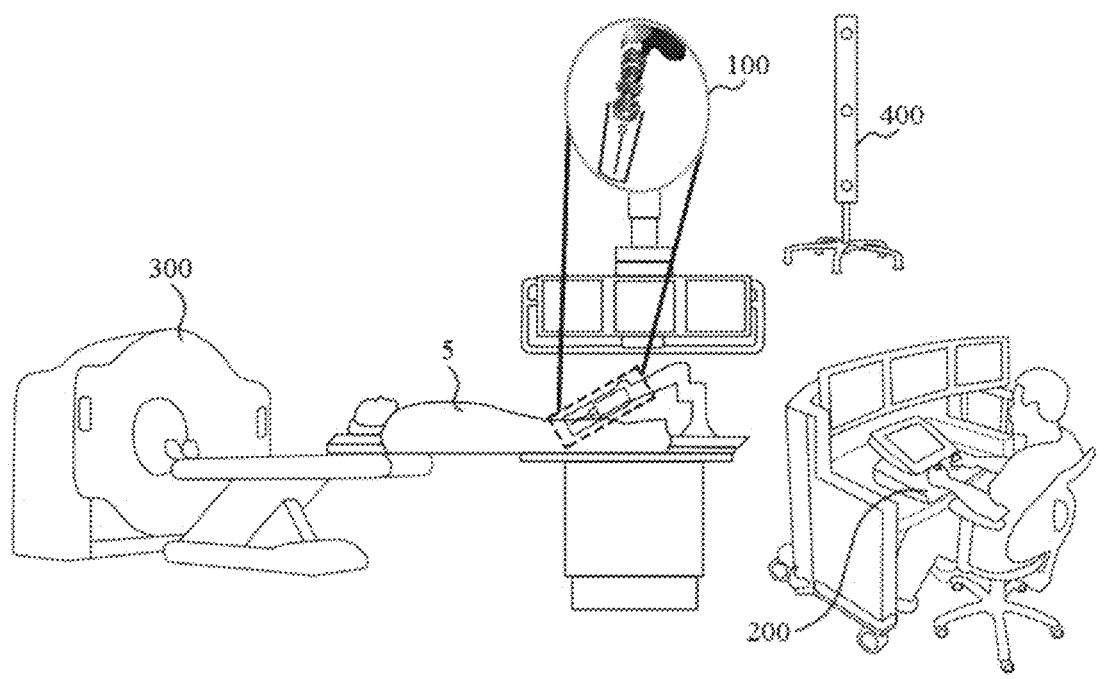
FIG. 25 shows an example of a system for interventional procedures, employing a robot for interventional procedures including needle insertion according to the present disclosure.

FIG. 25 shows an example of a system for interventional procedures, employing a robot for interventional procedures including needle insertion according to the present disclosure.

A robot 100 for interventional procedures including needle insertion can reduce radiation exposure, and may be used in a robotic system for a biopsy and image-guided interventional procedures including needle insertion for therapeutic purposes, in order to accomplish an improved accuracy of surgical operations. The robot for interventional procedures including needle insertion may also be used for a biopsy and treatment of lesions smaller than 1 cm found in the abdomen, the chest and so on.

For example, the robotic system for interventional procedures including needle insertion can include, for example, a high-reliability, high-precision robot for interventional procedures including needle insertion, a master device 200 for real-time control of the robot for interventional procedures including needle insertion, a device 300 for imaging the location of a surgical device inside the body, and a device 400 for monitoring the location and posture of a patient 5. Here, the robot 100 for interventional procedures including needle insertion is a slave robot, and a surgical tool to be installed at an arm of the robot is not particularly limited to a needle-type surgical tool. If a needle-type surgical tool is installed at the slave robot, the robot hereinafter will be referred to as a robot 100 for interventional procedures including needle insertion.

Figure 26:
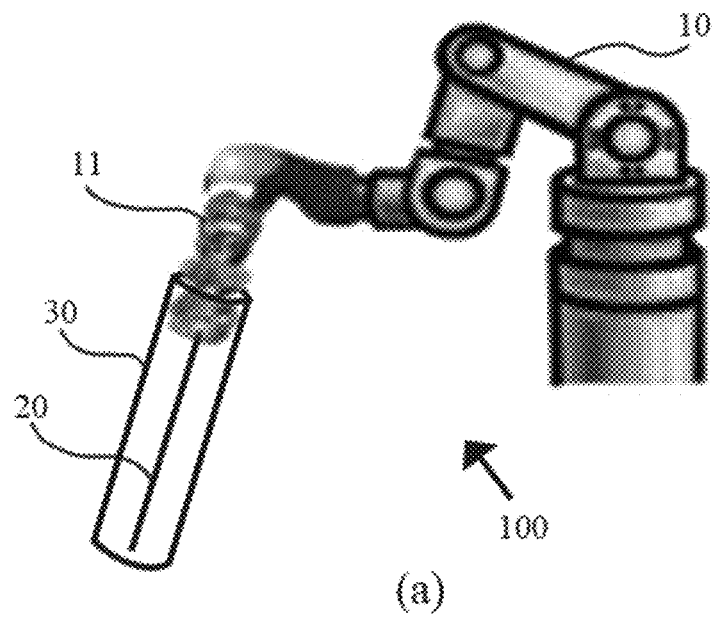
FIG. 26(a) shows an example of a state where a needle-type surgical tool is covered up.
FIG. 26(b) shows an example of a state where a needle-type surgical tool is exposed.
Figure 26:
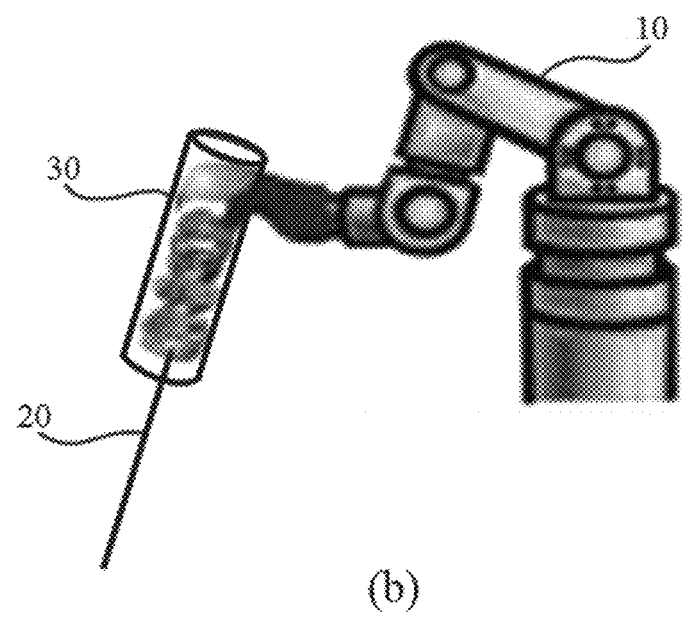

FIG. 26(*a*) shows an example of a state where a needle-type surgical tool is covered up, and FIG. 26(*b*) shows an example of a state where a needle-type surgical tool is exposed.

The robot 100 for interventional procedures including needle insertion includes a robot arm 100, a needle-type surgical tool 20, and a protection module 30. The robot arm 10 is provided with a location around the patient 4, in response to an externally applied control signal. The robot arm 10 has an axis for controlling a position of the robot arm, an axis for determining a spatial position, and an axis for controlling posture, and may be configured to be able to rotate horizontally and back and forth.

The needle-type surgical tool 20 can be installed at the robot arm 10, by either being installed directly at the robot arm or via the protection module 30. The protection module 30 is installed at the robot arm 10, for example, at a posture control unit 11 of the robot arm. When the needle-type surgical tool 20 is being carried by the robot arm, the protection module 30 hides the needle-type surgical tool 20 from the view or sight of the patient 5 as illustrated in FIG. 26(*a*); when the needle-type surgical tool 20 is aligned with a target in the patient 5 (e.g. a biopsy tissue sample), the needle-type surgical tool 20 may be exposed as illustrated in FIG. 26(*b*).

One optional way is that the needle-type surgical tool 20 is fixed to the robot arm 10, and the protection module 30 moves to hide the needle-type surgical tool 20 from the sight of the patient 5. Alternatively, the protection module 30 may be fixed to the robot arm 10, and the needle-type surgical tool 20 moves in such a manner that the needle-type surgical tool 20 is covered up with the protection module 30. More details on the structures of the needle-type surgical tool 20 and the protection module 30 are provided below.

As aforementioned, the protection module 30 hides the needle-type surgical tool 20 from the sight of the patient 5 until the needle-type surgical tool 20 is aligned with a target in the patient 5. In this way, the fear of the patient 5 experienced by such a needle-type surgical tool can be reduced, and it is possible to prevent possible contacts, infections or contaminations between the needle-type surgical tool 20 and an operator, an assistant, peripheral devices, etc.

Figure 27:
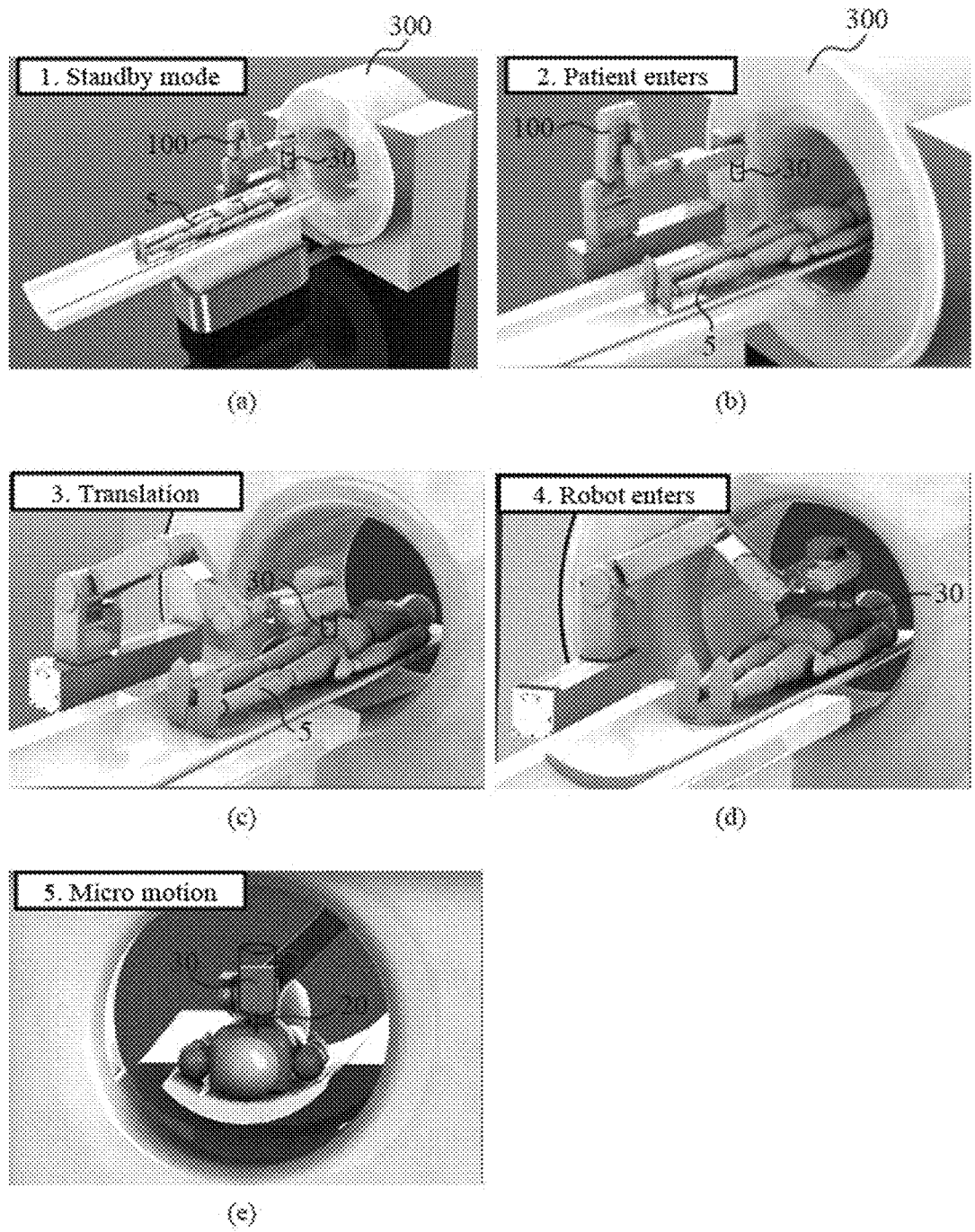
FIG. 27 shows an example of actions of a robot for interventional procedures including needle insertion.

FIG. 27 shows an example of actions of a robot for interventional procedures including needle insertion.

The needle-type surgical tool 20 includes medical devices such as a biopsy needle, a lead for DBS, a probe, a catheter or the like. The following description will be given with respect to a biopsy needle.

For instance, the robot 100 for interventional procedures including needle insertion is set in standby mode as shown in FIG. 27(a). Here, the biopsy needle 20 and the protection module 30 are already loaded in the robot 100 for interventional procedures including needle insertion. The biopsy needle 20 can be hidden from the sight of the patient 5 by the protection module 30. Then, the patient 5 is led into an imaging system such as a CT 300 as shown in FIG. 27(b), and the robot 100 for interventional procedures including needle insertion is translated towards a CT gantry and positioned in place, as shown in FIG. 27(c). The robot 100 for interventional procedures including needle insertion enters in the CT gantry and is positioned as shown in FIG. 27(d). Until this point, the biopsy needle 20 is hidden from the sight of the patient 5 by the protection module 30, such that the patient 5 may not become fearful and contamination of the needle due to a contact can be avoided. The biopsy needle 20 is aligned with the target in the patient 5 as shown in FIG. 27(e). For instance, the biopsy needle 20 that has been covered up by the protection module 30 is now exposed in order to get aligned at a place 1 cm away from an entry point on the skin of the patient 5. Once the biopsy needle 20 is pierced into the entry point for a biopsy and then taken out after the biopsy is completed, the biopsy needle 20 is covered up with the protection module 30 and then taken away from the patient 5, being still covered up, and eventually it gets out of the CT gantry. The biopsy result can be obtained from the biopsy needle 20, and the biopsy needle 20 and the protection module 30 can be detached, together or separately, from the robot 100 for interventional procedures including needle insertion.

The protection module 30 is designed to have a compact size such that it does not create inconvenience or discomfort to the CT gantry or the patient 5 in the course of the interventional procedures. Also, it is installed at the robot arm in an attachable/detachable manner by suitable mechanism, thereby easily moving around. During a biopsy, however, it is important that the protection module 30 is shifted into its proper position not to interfere with the biopsy. Sometimes, blood may spatter during the biopsy or when the biopsy needle 20 is separated from the skin. If this occurs, the protection module 30 covers up the biopsy needle 20 and further to protect the system, thereby preventing contaminations or infections. As the biopsy needle 20 stained with blood is shielded and detached all together at once, nurses or surgeons may be perfectly safe from being pricked with the needle or being infected.

Figure 28:
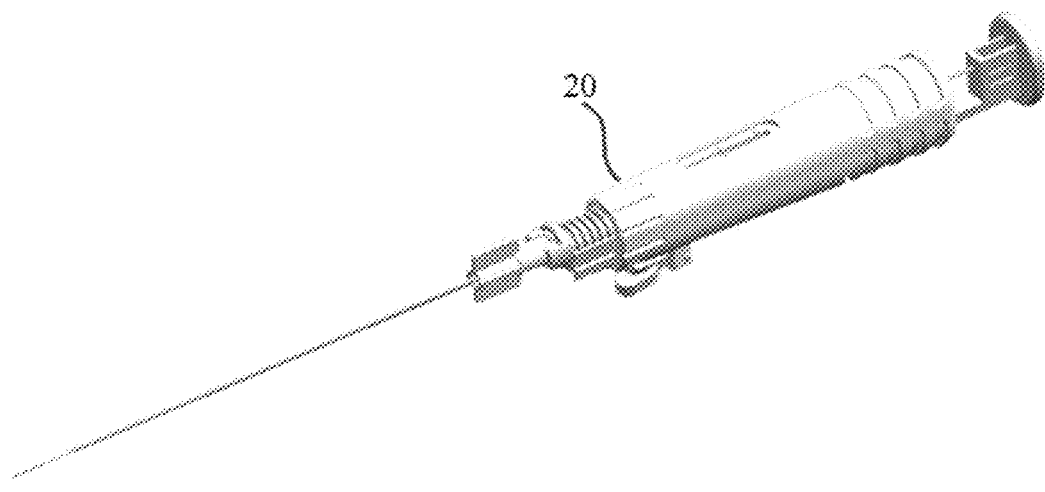
FIG. 28 shows examples of a needle-type surgical tool.
Figure 28:
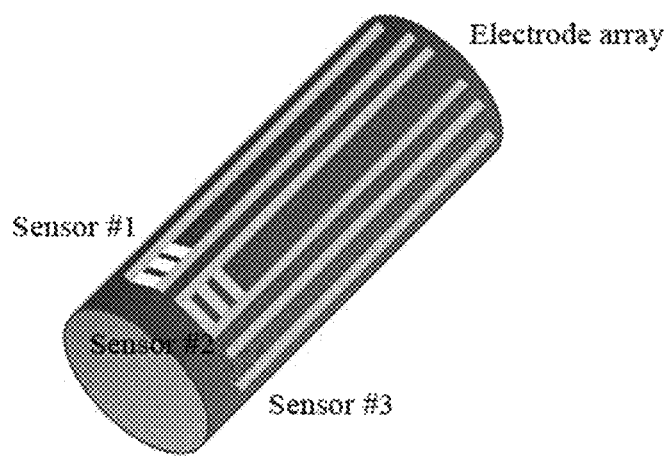

FIG. 28 shows examples of a needle-type surgical tool.

In this example, the needle-type surgical tool 20 means any tool that is inserted into a target in the patient 5. Therefore, it is not particularly limited to ones like needles. For instance, the surgical tool may be a biopsy needle 20 as depicted in FIG. 28(a) or a DBS lead electrode as depicted in FIG. 28(b). The biopsy needle 20 may include a needle and a body for discharging the needle. In the present disclosure, the biopsy needle 20 in FIG. 28(a) is introduced for illustrative purposes only. In another example, the needle-type surgical tool may include a biopsy needle and a drive unit adapted to take the biopsy needle into or out of the protection module 30

Figure 29:
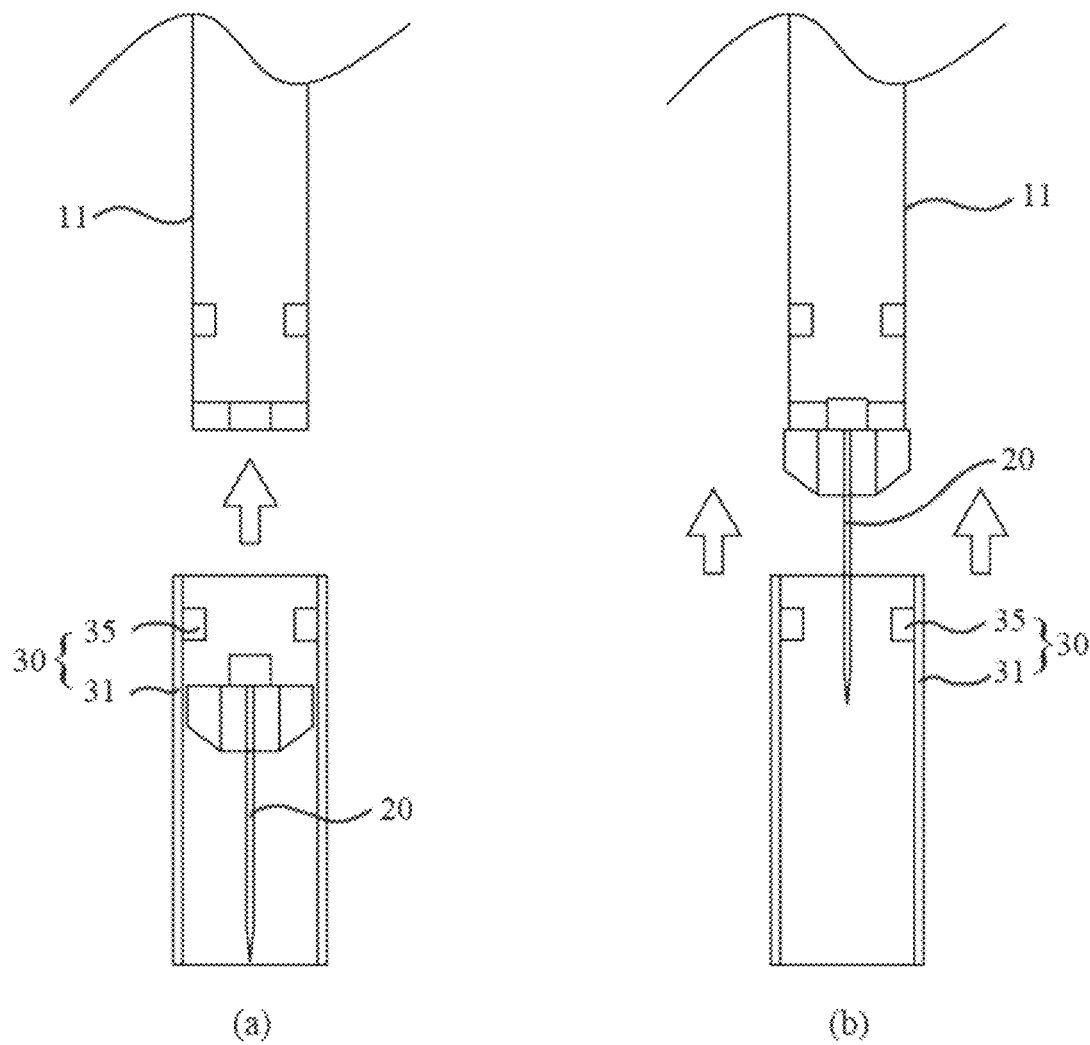
FIG. 29 shows examples of different schemes for connecting a protection module to a robot arm.

FIG. 29 shows examples of different schemes for connecting a protection module to a robot arm.

The protection module 30 may include a protection cover 31 and a drive unit 35. The protection cover 31 may be formed in a barrel-shaped cylinder, and have a structure where part of its side is open to reduce interference when the protection cover 31 is installed at the biopsy needle 20 or the posture control unit 11 of the robot arm 10. The protection cover 31 may be made out of materials such as plastic or metals. The drive unit 35, which is provided in the protection cover 31, may include a power transfer mechanism (e.g., a motor) driven by external power means. The biopsy needle 20 is either installed inside the protection cover 31 as shown in FIG. 29(a), or installed at the posture control unit 11 of the robot arm 10, independently of the protection cover 31, as shown in FIG. 29(b).

Figure 30:
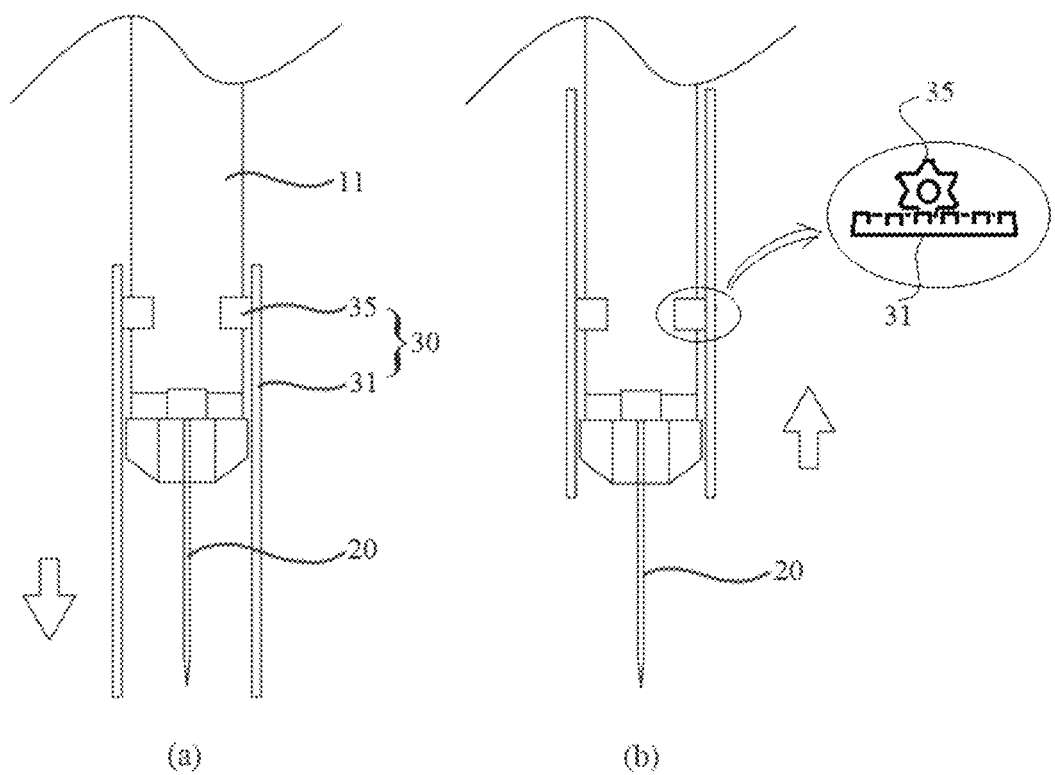
FIG. 30 shows an example of an operational mode of the protection module.

FIG. 30 shows an example of an operational mode of the protection module.

The drive unit 35 can move the protection cover 31 in the vertical direction along the posture control unit 11 of the robot arm 10, in response to a control signal transmitted from outside (e.g., a master device). Also, the drive unit 35 can make the protection cover 31 slide on the posture control unit 11 of the robot arm 10. To this end, the posture control unit 11 may have a rail or groove formed thereon to guide the protection cover 31. The drive unit 35 may be transformed in diverse ways by adopting different locations, power transmission modes, connecting means with the protection cover 31 and so on. For instance, as shown in FIG. 30(b), the drive unit 35 may have a motor and a gear connected to the motor. The protection cover 31 may have teeth which engage and mesh with the teeth of the gear. If the biopsy needle 20 and the protection module 30 are installed at the robot arm as one body, they can be detached from the robot arm 10 together as well. Besides those illustrated in FIG. 26 through FIG. 30, there are more diverse methods for installing the protection module 30 and the biopsy needle 20 at the robot arm 10. In this example, the biopsy needle 20 and the protection module 30 may serve as a basic needle-inserting end effector.

Figure 31:
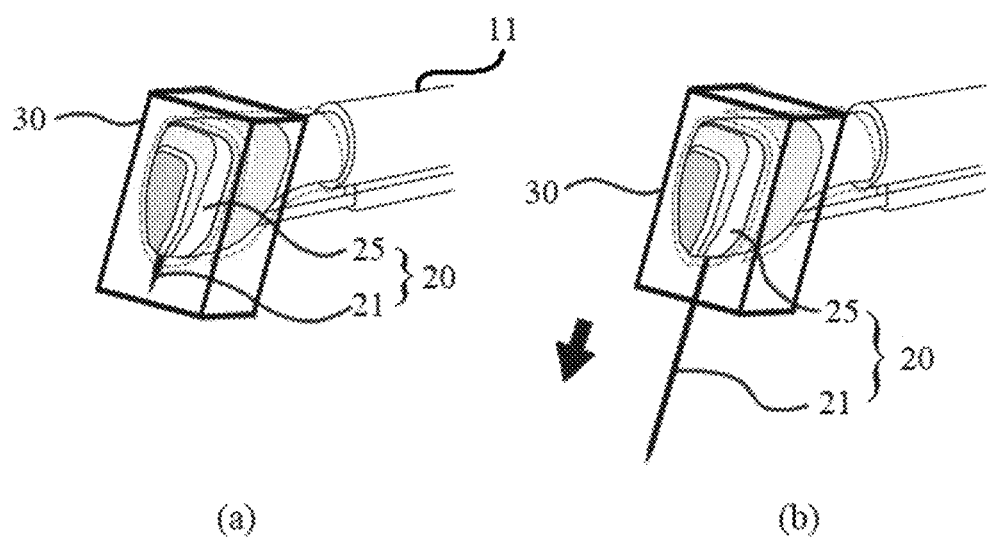
FIG. 31 shows a further example of a robot for interventional procedures including needle insertion according to the present disclosure.

FIG. 31 shows a further example of a robot for interventional procedures including needle insertion according to the present disclosure.

In this example, the protection module 30 is a barrel or protection cover for accommodating the needle-type surgical tool 20 inside. The needle-type surgical tool 20 can include a biopsy needle 21 and a drive unit 25. As described earlier with reference to FIG. 27, the biopsy needle 21 is kept covered up in the protection module 30 as depicted in FIG. 31(a) until the biopsy needle 21 is aligned with a target in the patient 5. Once the biopsy needle 21 is aligned with a target in the patient 5, the drive unit 25 moves the biopsy needle 21 to be exposed out of the protection module 30. The biopsy needle 21 is then discharged towards an entry point, or the biopsy needle 21 is gently manipulated by the posture control unit 11 of the robot arm and pricks the entry point of the patient 5. Once the biopsy needle 21 is taken out of the entry point, the drive unit 25 moves the biopsy needle 21 into the protection module 30 to hide it, such that the robot arm 10 may become free to move.

Figure 32:
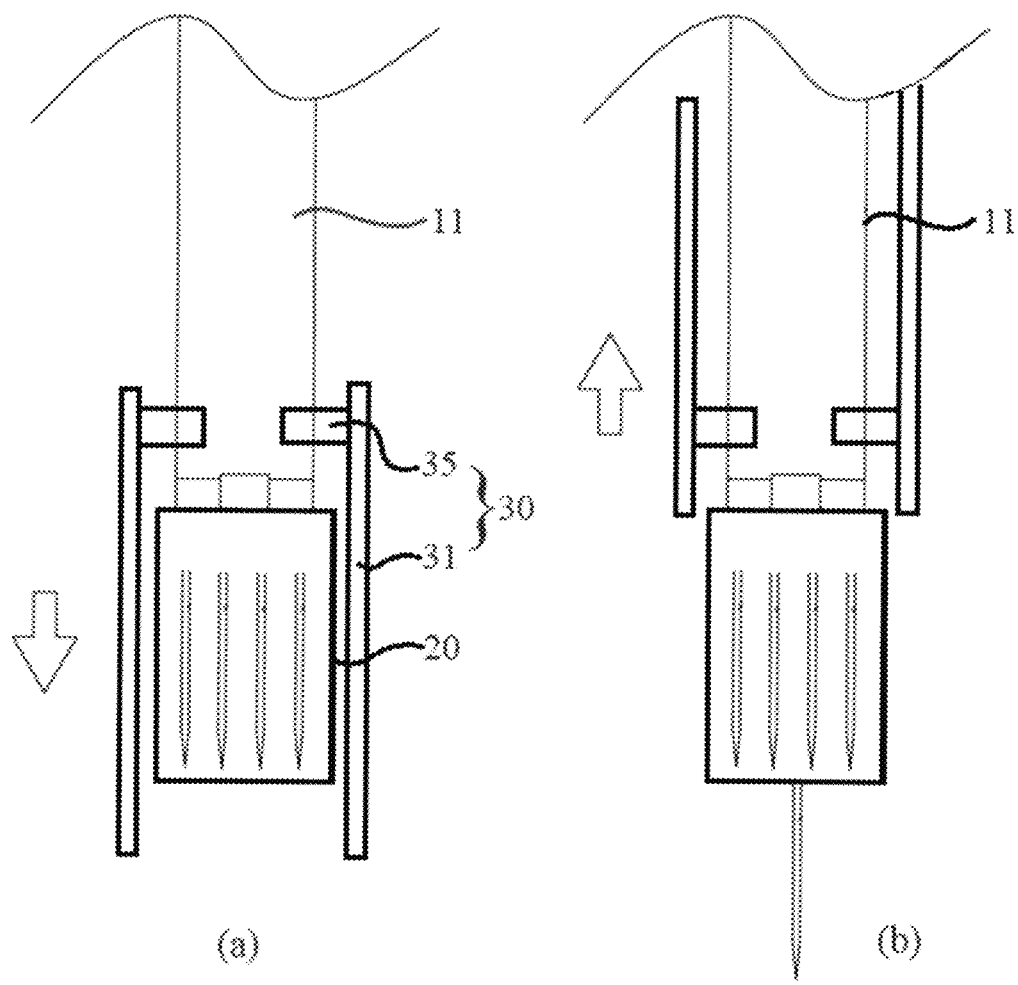
FIG. 32 shows a further example of a robot for interventional procedures including needle insertion according to the present disclosure.

FIG. 32 shows a further example of a robot for interventional procedures including needle insertion according to the present disclosure.

In this example, the protection module 30 is a separate or independent part from the biopsy needle 20, and includes a protection cover and a drive unit installed at the posture control unit 11 of the robot arm 10. The needle-type surgical tool 20 is installed at the posture control unit 11 of the robot arm 10, and may include at least one biopsy needle. For instance, the needle-type surgical tool 20 may be a cartridge containing multiple biopsy needles therein. This type of cartridge itself may cause discomfort and disgust to some patients. The protection cover while in motion blocks the biopsy needle cartridge 20 from the sight of the patient as shown in FIG. 32(a). When the biopsy needle is aligned with an entry point in the patient, the protection cover moves to expose the biopsy needle cartridge as shown in FIG. 32(b), thereby allowing the biopsy needle to emerge.

Figure 33:
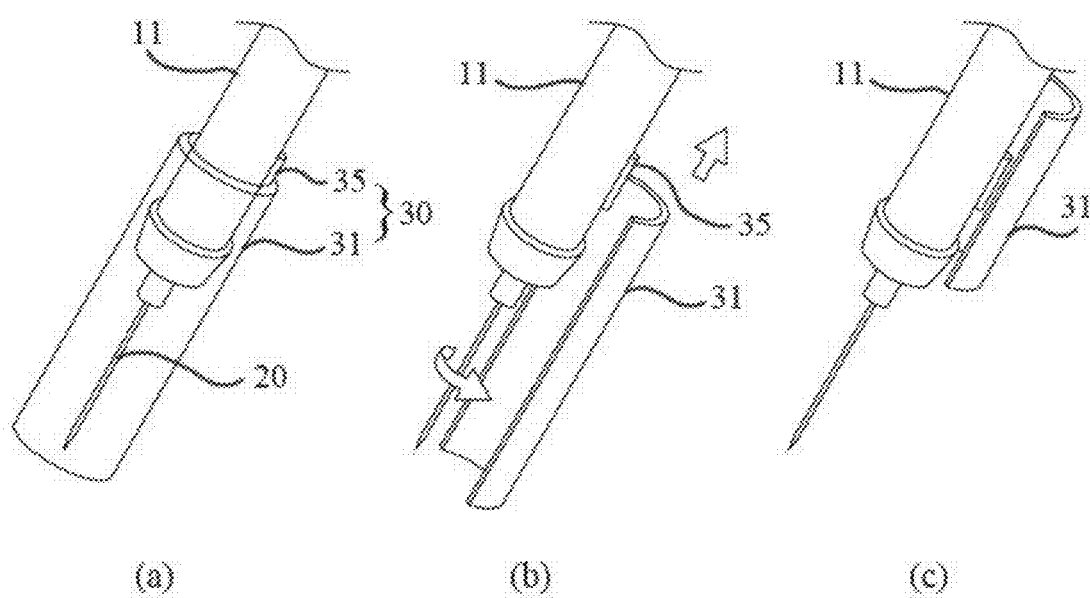
FIG. 33 shows a further example of a robot for interventional procedures including needle insertion according to the present disclosure.

FIG. 33 shows a further example of a robot for interventional procedures including needle insertion according to the present disclosure.

In this example, the protection module 30 includes a protection cover 31 and a drive unit 35. Referring to FIG. 33(a), the protection cover 31 is installed at the posture control unit 11 of the robot arm and cover the biopsy needle 20. The drive unit 35 may be arranged at one side of the protection cover 31 and coupled to the posture control unit 11. In this example, the protection cover 31 rotates with respect to the biopsy needle 20, for example, thereby exposing the biopsy needle as shown in FIG. 33(b), and then slides back as shown in FIG. 33(c) into its place to avoid interference with the biopsy needle 20 during a biopsy. When the biopsy is over, the biopsy needle 20 can be covered up again, following the above process in an inverse order.

Figure 34:
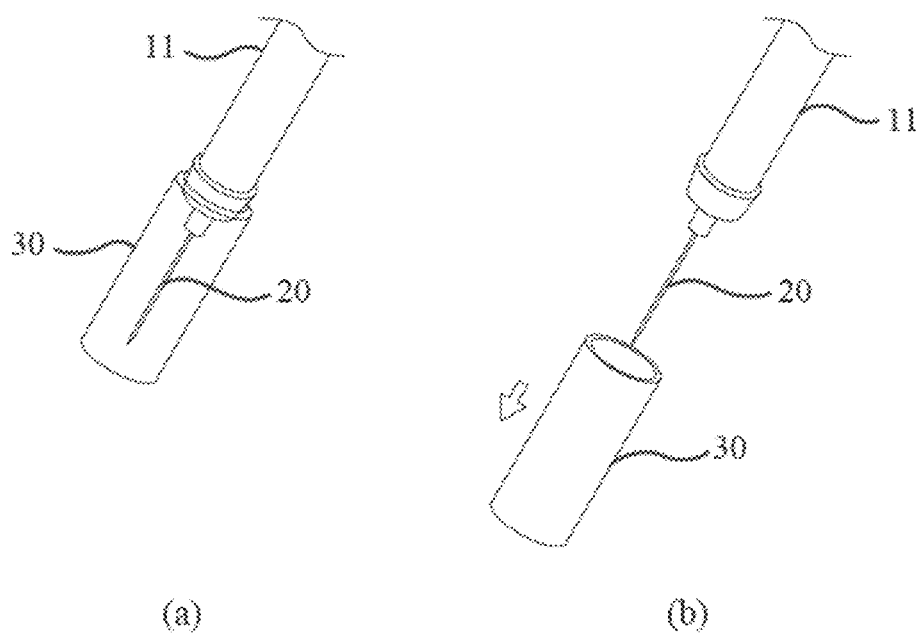
FIG. 34 shows a further example of a robot for interventional procedures including needle insertion according to the present disclosure.

FIG. 34 shows a further example of a robot for interventional procedures including needle insertion according to the present disclosure.

In this example, the protection module 30 is a cap adapted to accommodate the needle portion of the biopsy needle 20. The cap is connected to the posture control unit 11 of the robot arm or to the biopsy needle 20 in such a manner that it covers the biopsy manner 20 as shown in FIG. 34(a), and the cap may be taken off manually to expose the biopsy needle 20 as shown in FIG. 34(b). When the robot 100 for interventional procedures is aligned with a target in the patient 5, an assistant of an interventional procedure, for example, can take off the cap using a hand, and put it back to cover up the biopsy needle 20 after a biopsy is over.

Figure 35:
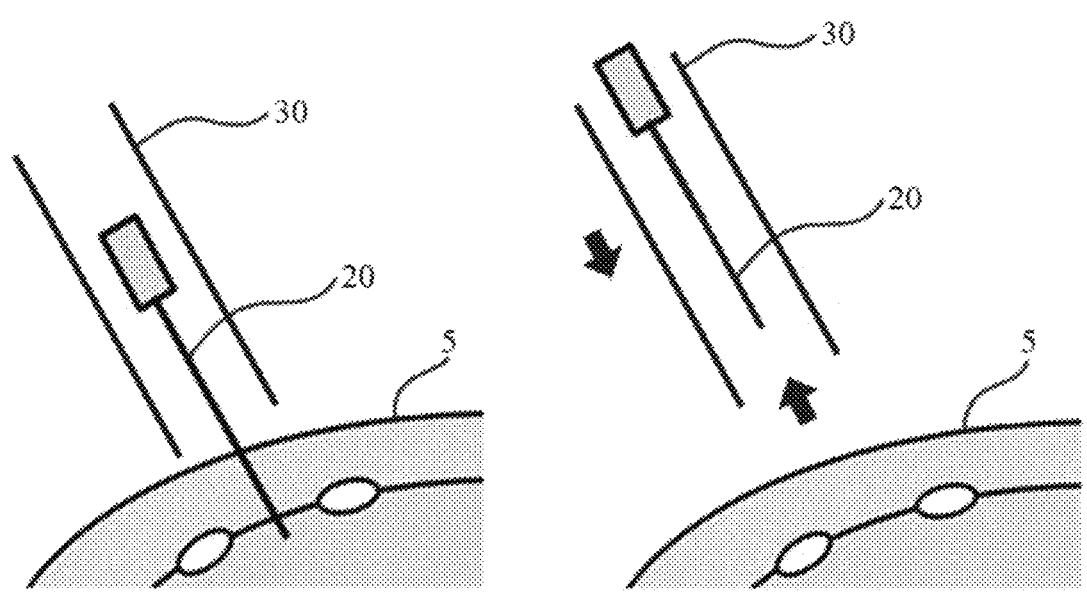
FIG. 35 shows an example of an operational mode of a robot for interventional procedures including needle insertion according to the present disclosure.

FIG. 35 shows an example of an operational mode of a robot for interventional procedures including needle insertion according to the present disclosure.

When the biopsy needle 20 approaches towards the patient 5, it is covered up with the protection cover 31 and hidden from the sight of the patient 5, so as to reduce the fear caused to the patient 5. Once the biopsy needle 20 is aligned with a target in the patient 5, however, the protection cover 31 is lifted up and the biopsy needle 20 is then exposed. While a biopsy is being performed after the biopsy needle 20 was inserted, the protection cover 31 again covers up the surrounding area of the biopsy needle 20 as shown in FIG. 35(a), in order to avoid blood spattering or other possible contaminations. When the biopsy needle 20 gets out, it is again covered up with the protection cover 31 and shifted together as shown in FIG. 35(b). With this movement, the biopsy needle 20 stained with blood cannot contaminate or infect people or devices around. In addition, as the biopsy needle 20 is detached together with the protection module 30 from the robot arm for handling, everyone can be perfectly safe from being accidently stuck by the needle.

Various exemplary embodiments of the present disclosure will now be described below.

(1) A method for generating an insertion trajectory of a surgical needle from an entry point to a target, comprising the steps of: preparing a medical image including the target and an anatomical structure; and extracting an insertion trajectory in consideration of at least one of a degree of invasion into the anatomical structure through the insertion trajectory and a distance of the insertion trajectory.

(2) The method for generating an insertion trajectory of a surgical needle from an entry point to a target, characterized in that the step of extracting an insertion trajectory includes the insertion trajectory is extracted in consideration of a distance of the insertion trajectory with a weighing value applied thereto, and a distance between the insertion trajectory with a weighing value applied thereto and the anatomical structure.

(3) The method for generating an insertion trajectory of a surgical needle, characterized in that the step of extracting an insertion trajectory includes at least one of the following: a process of extracting an insertion trajectory that has a weighing value 0 for a distance of the insertion trajectory and a minimal degree of invasion; and a process of extracting an insertion trajectory that has a weighing value 0 for the degree of invasion and a shortest distance, wherein the process of extracting an insertion trajectory that has a weighing value 0 for a distance of the insertion trajectory and a minimal degree of invasion can imply the insertion trajectory does not intersect with an anatomical structure.

(4) The method for generating an insertion trajectory of a surgical needle from an entry point to a target, characterized in that the step of extracting an insertion trajectory includes: a process of extracting an insertion trajectory having a degree of invasion within an allowable limit; and a process of extracting an insertion trajectory having a shortest distance for the insertion trajectory among the insertion trajectories having degree of invasion within an allowable limit.

(5) The method for generating an insertion trajectory of a surgical needle from an entry point to a target, characterized in that the step of extracting an insertion trajectory includes multiple insertion trajectories are extracted, and the multiple insertion trajectories form a cone shape having a progressively diminishing cross-section towards the target.

(6) The method for generating an insertion trajectory of a surgical needle from an entry point to a target, characterized in that the step of preparing a medical image includes: a process of segmenting an anatomical structure included in a lung image; a process of generating a distance map of the anatomical structure using the segmented lung image; and a process of selecting a target from the segmented lung image.

(7) The method for generating an insertion trajectory of a surgical needle from an entry point to a target, characterized in that the process of generating a distance map of the anatomical structure includes a process of generating a distance map of lung boundary, a distance map of rib, a distance map of pulmonary vessel, and a distance map of airway, and in the step of extracting an insertion trajectory in consideration of at least one of a degree of invasion into the anatomical structure through the insertion trajectory and a distance of the insertion trajectory, an angle ($\phi$) of the insertion trajectory satisfying the equation below is generated:

$$\operatorname*{argmin}_{\phi} f(\phi) = w_1 \sum D_{lung} + w_2 \sum D_{airway} + w_3 \sum D_{vessel} + w_4 \sum D_{rib}$$

where $D_{rib} + \varphi < 0 \rightarrow D_{rib} = \infty$ where Dlung denotes a distance of the insertion trajectory from the entry point to the target; Dairway, Dvessel and Drib denotes distances from the insertion trajectory to airway, vessel and rib, respectively, on the distance map; and w1, w2, w3 and w4 are weighing values.

(8) The method for generating an insertion trajectory of a surgical needle from an entry point to a target, characterized in that the step of extracting an insertion trajectory includes: a process of calculating the number and thickness of vessels that intersect with the insertion trajectory, from the target included in a 3D lung image by ray casting; and a process of calculating a shorted distance from the entry point to the target of the insertion trajectory using the distance map of lung boundary of the 3D lung image.

(9) The method for generating an insertion trajectory of a surgical needle from an entry point to a target, characterized in that further comprising the steps of: matching a lung image having an insertion trajectory generated with a lung image at a surgery site; and defining a safety margin within a certain distance away from the anatomical structure, in which the insertion trajectory is not allowed to pass, and excluding an insertion path that is close to the safety margin from the anatomical structure during breathing, in the insertion trajectory transferred onto the matched lung image at a surgery site.

(10) The method for generating an insertion trajectory of a surgical needle from an entry point to a target, characterized in that the step of preparing a medical image includes: a process of extracting a vessel as a 3D set of voxels based on an initial lung image generated from a medical imaging apparatus; a process of constructing an initial lung vessel tree by applying a minimum spanning tree method to a lung vessel included in the initial lung image; a process of separating the initial lung vessel tree into sub-trees in an automated manner by removing a mediastinal region of clogged lung vessel from the initial lung vessel tree; a process of merging the sub-trees by extending the lung vessel of the initial tree into the removed mediastinal region; and a process of constructing a classified lung vessel tree by classifying the lung vessels in the merged initial tree into lung artery and lung vein; and wherein the step of extracting an insertion trajectory includes: a process of calculating the number and thickness of vessels where the classified lung vessel tree intersects with the insertion trajectory, by performing 3D ray casting on the target included in a 3D lung image; and a process of calculating a shortest distance from the entry point to the target using a distance map of lung boundary in the 3D lung image.

(11) A method for generating an insertion trajectory of a medical device from an entry point to a target, characterized by including the steps of: preparing a surgical target image including the target and an invasion prohibited region; designating an initial entry region including an insertion trajectory, in which the initial entry region has a 3D truncated column having a progressively diminishing cross-section towards the target; deciding whether the initial entry region and the invasion prohibited region intersect each other; and generating a safe entry region by diminishing the initial entry region to avoid an intersection, wherein the invasion prohibited region indicates a region where an anatomical structure including a vessel for example is included, and the medical device includes a surgical needle.

(12) The method for generating an insertion trajectory of a medical device from an entry point to a target, characterized in that the step of designating an initial entry region includes a process of defining an initial entry region from an entry range to a target, in which the entry range is designated on the surface of the target shown on the target image.

(13) The method for generating an insertion trajectory of a medical device from an entry point to a target, characterized in that the step of deciding whether the initial entry region and the invasion prohibited region intersect each other includes a process of calculating a distance from the boundary of the initial entry region to the invasion prohibited region.

(14) The method for generating an insertion trajectory of a medical device from an entry point to a target, characterized in that the step of preparing a target image includes a process of segmenting the invasion prohibited region including a vessel using sagittal, axial and coronal view images of the target acquired from a medical imaging apparatus; and a process of performing volume alignment on the images.

(15) The method for generating an insertion trajectory of a medical device from an entry point to a target, characterized in that the target is a stimulation target in Deep Brain Stimulation (DBS).

(16) The method for generating an insertion trajectory of a medical device from an entry point to a target, characterized in that the step of preparing a surgical target image includes: a process of segmenting the invasion prohibited region including a vessel, using brain images in sagittal, axial and coronal views acquired from a medical imaging apparatus; and a process of performing volume alignment on the brain images with respect to an anterior commissure-posterior commissure line, and that the step of designating an initial entry region includes a process of designating a truncated cone shaped initial entry region from an entry range to the target by designating the entry range in form of a curved surface using at least two of the aligned brain images in sagittal, axial and coronal views.

(17) The method for generating an insertion trajectory of a medical device from an entry point to a target, characterized in that the step of preparing a target image includes: a process of segmenting the invasion prohibited region including a vessel into a 3D set of voxels using brain images in sagittal, axial and coronal views acquired form a medical imaging apparatus; and a process of performing volume alignment on the segmented brain images with respect to an anterior commissure-posterior commissure line, and that the step of deciding whether the initial entry region and the invasion prohibited region intersect each other includes a process of generating a distance map, by ray casting, from the boundary of an initial entry region to the voxels of the invasion prohibited region.

(18) The method for generating an insertion trajectory of a medical device from an entry point to a target, characterized in that the step of generating a safe entry region includes: a process of cone fitting the safe entry region obtained from the diminished initial entry region outside a safety margin from the invasion prohibited region using a distance map; and a process of extracting an entry point from intersection points between the central line in the safe entry region and the head surface shown in the brain images.

(19) The method for generating an insertion trajectory of a medical device from an entry point to a target, characterized by including the step of: displaying brain images as seen through a virtual camera which is arranged at the medical device, along an insertion trajectory from the entry point to the target.

(20) The method for generating an insertion trajectory of a medical device from an entry point to a target, characterized in that the step of preparing a surgical target image includes: a process of segmenting the invasion prohibited region including a vessel, using brain images in sagittal, axial and coronal views acquired from a medical imaging apparatus; and a process of performing volume alignment on the brain images with respect to an anterior commissure-posterior commissure line, and that the step of designating an initial entry region includes a process of designating a truncated cone shaped initial entry region from an entry range to the target by designating the entry range in form of a curved surface using at least two of the aligned brain images in sagittal, axial and coronal views, and that the step of deciding whether the initial entry region and the invasion prohibited region intersect each other includes a process of generating a distance map, by ray casting, from the boundary of an initial entry region to the voxels of the invasion prohibited region, and that the step of generating a safe entry region includes: a process of cone fitting the safe entry region obtained from the diminished initial entry region outside a safety margin from the invasion prohibited region using a distance map; and a process of extracting an entry point from intersection points between the central line in the safe entry region and the head surface shown in the brain images.

(21) A robot for interventional procedures including needle insertion, characterized by including: a robot arm to be positioned near a patient, in response to an externally applied control signal; a needle-type surgical tool to be carried by the robot arm; and a protection module installed at the robot arm and adapted to cover up the needle-type surgical tool from sight of the patient.

(22) The robot for interventional procedures including needle insertion, characterized in that the needle-type surgical tool is kept covered up with the protection module until the needle-type surgical tool is aligned with an entry point in a patient present in a medical imaging apparatus, and the needle-type surgical tool is exposed from the protection module after the needle-type surgical tool is aligned with the entry point.

(23) The robot for interventional procedures including needle insertion, characterized in that the protection module and the needle-type surgical tool are installed at the robot arm as one body being connected together, and the protection module includes: a protection cover for accommodating the needle-type surgical tool; and a drive unit adapted to move the protection cover such that the needle-type surgical tool is covered up or exposed during movement of the robot arm.

(24) The robot for interventional procedures including needle insertion, characterized in that the protection module and the needle-type surgical tool are installed at the robot arm as one body being connected together, and he protection module includes: a protection cover for accommodating the needle-type surgical tool; and a drive unit adapted to move the needle-type surgical tool to take the tool into or out of the protection cover.

(25) The robot for interventional procedures including needle insertion, characterized in that the protection module and the needle-type surgical tool are installed as separate parts at the robot arm, and the protection module includes: a protection cover installed at the robot arm; and a drive unit installed at the robot arm and adapted to move the protection cover for covering up or exposing the needle-type surgical tool.

(26) The robot for interventional procedures including needle insertion, characterized in that the protection module and the needle-type surgical tool are installed as separate parts at the robot arm, and the needle-type surgical tool includes: a surgical needle installed at the robot arm; and a drive unit installed at the robot arm and adapted to move the surgical needle in such a manner that the needle-type surgical tool is covered up with the protection module or exposed from the protection module.

(27) The robot for interventional procedures including needle insertion, characterized in that the protection cover slides over the robot arm by the drive unit.

(28) The robot for interventional procedures including needle insertion, characterized in that the protection cover rotates by the drive unit with respect to the needle-type surgical tool, so as to cover up or expose the needle-type surgical tool.

(29) The robot for interventional procedures including needle insertion, characterized in that the needle-type surgical tool includes a surgical needle, and the protection cover includes a cap connected to the needle-type surgical tool, so as to accommodate the needle therein.

(30) The robot for interventional procedures including needle insertion, characterized in that the drive unit is adapted to move the protection cover in such a manner that the protection cover covers up an area around the entry point when the needle-type surgical tool is inserted into a patient, and that the protection cover covers up the needle-type surgical tool when the tool is being taken out of the patient.

In one aspect of the method for generating an insertion trajectory of a surgical needle according to the present disclosure, it is possible to generate an insertion trajectory resulting from objective and quantitative bases for at least one of minimal invasion and shortest distance.

In another aspect of the method for generating an insertion trajectory of a surgical needle according to the present disclosure, it is possible to reduce the degree of invasion into a vessel for example during an operation like a biopsy using a surgical needle, such that the risks involved with the needle can be reduced.

In a further aspect of the method for generating an insertion trajectory of a surgical needle according to the present disclosure, an insertion trajectory obtained in consideration of at least one of minimal invasion and shortest distance is automatically generated, such that user convenience can be improved.

In a further aspect of the method for generating an insertion trajectory of a surgical needle according to the present disclosure, a 3D insertion trajectory thus generated overcomes the limits on conventional methods of planning and guiding an insertion trajectory on a 2D cross-section.

In an aspect of the method for generating an insertion trajectory of a medical device according to the present disclosure, an insertion trajectory thus generated has objective and quantitative bases in terms of avoiding an invasion prohibited region including a vessel or a ventricle.

In another aspect of the method for generating an insertion trajectory of a medical device according to the present disclosure, it is possible to reduce risks by avoiding invasion into a vessel for example during an operation (e.g. DBS) using a medical device.

In a further aspect of the method for generating an insertion trajectory of a medical device according to the present disclosure, an insertion trajectory without interfering with an invasion prohibited region can be generated in an automated manner under conditions set by a user, such that user convenience can be improved.

In a further aspect of the method for generating an insertion trajectory of a medical device according to the present disclosure, a 3D insertion trajectory thus generated overcomes the limits on conventional methods of planning and guiding an insertion trajectory on a 2D cross-section.

In an aspect of the robot for interventional procedures including needle insertion according to the present disclosure, the fear of a patient is reduced as a needle-type surgical tool such as a biopsy needle is hidden from sight of the patient.

In another aspect of the robot for interventional procedures including needle insertion according to the present disclosure, a needle-type surgical tool such as a biopsy needle is covered up with a protection module, such that contaminations of the biopsy needle can be prevented, an operator or other people nearby can be protected from infection due to the biopsy needle, and contaminations of a medical device can be avoided.

What is claimed is:

1. A method for generating an insertion trajectory of a surgical needle from an entry point to a target, the method comprising:
    preparing a medical image including the target and an anatomical structure; and
    extracting an insertion trajectory in consideration of at least one of a degree of invasion into the anatomical structure through the insertion trajectory and a distance of the insertion trajectory, wherein the insertion trajectory is extracted in consideration of a distance of the insertion trajectory with a weighting value applied thereto and a distance from the insertion trajectory to the anatomical structure with a weighting value applied thereto.

2. The method according to claim 1, wherein extracting an insertion trajectory includes at least one of the following:
    extracting an insertion trajectory that has a weighting value 0 for a distance of the insertion trajectory and a minimal degree of invasion; and
    extracting an insertion trajectory that has a weighting value 0 for the degree of invasion and a shortest distance.

3. The method according to claim 1, wherein extracting an insertion trajectory includes:
    extracting insertion trajectories having a degree of invasion within an allowable limit; and
    extracting an insertion trajectory having a shortest distance for the insertion trajectory among the insertion trajectories having a degree of invasion within an allowable limit.

4. A method for generating an insertion trajectory of a surgical needle from an entry point to a target, the method comprising:
    preparing a medical image including the target and an anatomical structure; and
    extracting an insertion trajectory in consideration of at least one of a degree of invasion into the anatomical structure through the insertion trajectory and a distance to the insertion trajectory, wherein multiple insertion trajectories are extracted, and the multiple insertion trajectories form a cone shape having a progressively diminishing cross-section towards the target.

5. The method according to claim 1, wherein preparing a medical image includes:
    segmenting an anatomical structure included in a lung image;
    generating a distance map of the anatomical structure using the segmented lung image; and
    selecting a target from the segmented lung image.

6. The method according to claim 5, wherein generating a distance map of the anatomical structure includes generating a distance map of a lung boundary, a distance map of a rib, a distance map of a pulmonary vessel, and a distance map of an airway, and
    when extracting an insertion trajectory in consideration of at least one of a degree of invasion into the anatomical structure through the insertion trajectory and a distance of the insertion trajectory, an angle ($\phi$) of the insertion trajectory satisfying the equation below is generated:

$$\operatorname*{argmin}_{\phi} f(\phi) = w_1 \sum D_{lung} + w_2 \sum D_{airway} + w_3 \sum D_{vessel} + w_4 \sum D_{rib}$$

$$\text{where } D_{rib} + \varphi < 0 \rightarrow D_{rib} = \infty$$

where Dlung denotes a distance of the insertion trajectory from the entry point to the target; Dairway, Dvessel and Drib denotes distances from the insertion trajectory to airway, vessel and rib, respectively, on the distance map; and w1, w2, w3 and w4 are weighting values.

7. The method according to claim 5, wherein extracting an insertion trajectory includes:
    calculating the number and thickness of vessels that intersect with the insertion trajectory, from the target included in a 3D lung image by ray casting; and
    calculating a shortest distance from the entry point to the target of the insertion trajectory using the distance map of the lung boundary of the 3D lung image.

8. The method according to claim 5, further comprising:
    matching a lung image having an insertion trajectory generated with a lung image at a surgery site; and
    defining a safety margin within a certain distance away from the anatomical structure in which the insertion trajectory is not allowed to pass, and excluding an insertion path that is close to the safety margin from the anatomical structure during breathing, in the insertion trajectory transferred onto the matched lung image at a surgery site.

9. A method for generating an insertion trajectory of a surgical needle from an entry point to a target, the method comprising:
    preparing a medical image including the target and an anatomical structure; and
    extracting an insertion trajectory in consideration of at least one of a degree of invasion into the anatomical structure through the insertion trajectory and a distance of the insertion trajectory;
    wherein preparing the medical image includes:
    extracting a vessel as a 3D set of voxels based on an initial lung image generated from a medical imaging apparatus;
    constructing an initial lung vessel tree by applying a minimum spanning tree method to a lung vessel included in the initial lung image;
    separating the initial lung vessel tree into sub-trees in an automated manner by removing a mediastinal region of clogged lung vessel from the initial lung vessel tree;
    merging the sub-trees by extending the lung vessel of the initial tree into the removed mediastinal region; and of constructing a classified lung vessel tree by classifying the lung vessels in the merged initial tree into lung artery and lung vein; and wherein extracting an insertion trajectory includes:

calculating the number and thickness of vessels where the classified lung vessel tree intersects with the insertion trajectory, by performing 3D ray casting on the target included in a 3D lung image; and calculating a shortest distance from the entry point to the target using a distance map of lung boundary in the 3D lung image.

\* \* \* \* \*